US007476851B2

(12) United States Patent
Wang et al.

(10) Patent No.: US 7,476,851 B2
(45) Date of Patent: Jan. 13, 2009

(54) AERODYNAMIC FOCUSING OF NANOPARTICLE OR CLUSTER BEAMS

(75) Inventors: Xiaoliang Wang, St. Paul, MN (US); Peter H. McMurry, Minneapolis, MN (US); Einar Kruis, Emmerich am Rhein (DE)

(73) Assignee: Regents of the University of Minnesota, Saint Paul, MN (US)

( * ) Notice: Subject to any disclaimer, the term of this patent is extended or adjusted under 35 U.S.C. 154(b) by 228 days.

(21) Appl. No.: 11/269,932

(22) Filed: Nov. 9, 2005

(65) Prior Publication Data

US 2006/0102837 A1 May 18, 2006

Related U.S. Application Data

(60) Provisional application No. 60/627,576, filed on Nov. 12, 2004.

(51) Int. Cl.
*H01J 49/04* (2006.01)
*H01J 49/10* (2006.01)
*H01J 49/00* (2006.01)
*G01N 1/38* (2006.01)

(52) U.S. Cl. ........................ 250/288; 250/251; 73/23.2; 73/24.05; 73/31.04

(58) Field of Classification Search ................. 250/251, 250/288, 281, 282, 292; 73/23.2, 24.03, 73/24.04, 24.05, 25.04, 28.01–28.04, 29.01, 73/29.03, 31.04, 31.07
See application file for complete search history.

(56) References Cited

U.S. PATENT DOCUMENTS 3,854,321 A 12/1974 Dahneke
4,358,302 A 11/1982 Dahneke
4,801,411 A * 1/1989 Wellinghoff et al. ........... 264/7
4,863,491 A 9/1989 Brandt et al.
5,270,542 A * 12/1993 McMurry et al. ........... 250/288
5,453,306 A 9/1995 Tatsumi et al.
5,460,701 A 10/1995 Parker et al.
5,514,350 A 5/1996 Kear et al.
5,565,677 A 10/1996 Wexler et al.
5,874,134 A 2/1999 Rao et al.
6,156,212 A * 12/2000 Rader et al. ................. 210/788
6,259,101 B1 * 7/2001 Wexler et al. ............ 250/423 P
6,280,802 B1 8/2001 Akedo et al.
6,348,687 B1 * 2/2002 Brockmann et al. ......... 250/251
6,379,419 B1 4/2002 Celik et al.
6,387,531 B1 5/2002 Bi et al.
6,454,862 B1 * 9/2002 Yoshida et al. ............. 118/722

(Continued)

OTHER PUBLICATIONS

Zhang et al., "A Numerical Characterization of Particle Beam Collimation by an Aerodynamic Lens-Nozzle System: Part I. An Individual Lens or Nozzle", Aerosol Science and Technology 36:617-631 (2002).*

(Continued)

*Primary Examiner*—Bernard E Souw
(74) *Attorney, Agent, or Firm*—Fish & Richardson P.C.

(57) ABSTRACT

Guidelines for designing lenses or systems for aerodynamic focusing of nanoparticle or cluster beams. The design process may involve obtaining a relationship between particle size, operating pressure and aperture size, and selecting the operating pressure to provide continuum flow of an aerosol beam through the aerodynamic lens. Particles having diameters less than 30 nanometer may be focused. Simulation techniques for evaluating designed lenses are also disclosed.

34 Claims, 25 Drawing Sheets

U.S. PATENT DOCUMENTS

| | | | |
|---|---|---|---|
| 6,610,959 B2 | | 8/2003 | Carlson et al. |
| 6,809,314 B2 * | | 10/2004 | Yoshida et al. ............... 250/288 |
| 6,906,322 B2 * | | 6/2005 | Berggren et al. ............ 250/288 |
| 6,924,004 B2 * | | 8/2005 | Rao et al. ................. 427/421.1 |
| 6,972,408 B1 * | | 12/2005 | Reilly ......................... 250/292 |
| 7,078,679 B2 * | | 7/2006 | Westphall et al. ........... 250/287 |
| 7,097,902 B2 * | | 8/2006 | Blanton et al. .............. 428/330 |
| 7,141,783 B2 * | | 11/2006 | Kim et al. .................... 250/251 |
| 2002/0014441 A1 * | | 2/2002 | Yoshida et al. ........... 209/127.1 |
| 2002/0166961 A1 * | | 11/2002 | Berggren et al. ............ 250/288 |
| 2004/0046130 A1 * | | 3/2004 | Rao et al. ................. 250/492.1 |
| 2004/0169137 A1 * | | 9/2004 | Westphall et al. ........... 250/281 |
| 2005/0163917 A1 * | | 7/2005 | Renn ............................ 427/58 |
| 2006/0102837 A1 * | | 5/2006 | Wang et al. .................. 250/288 |
| 2008/0052904 A1 * | | 3/2008 | Schneider et al. ............. 29/846 |

OTHER PUBLICATIONS

"Factor of Safety" from Wikipedia, <http://en.wikipedia.org/wiki/Factor_of_safety>.*

"Vacuum technology: Flow, throughput, conductance, and pumping speed", <http://www.ecse.rpl.edu/~schubert/Course-Tracking-Modules/A17-Vacuum-pumps-and-pipes-pdf>.*

Fonzo et al., "Focused nanoparticle-beam deposition of patterned microstructures," *Applied Physics Letters*, Aug. 7, 2000, 77(6): 910-912.

De La Mora and Riesco-Chueca, "Aerodynamic focusing of particles in a carrier gas," *J. Fluid Mech*, May 16, 1987, 195: 1-21.

De la Mora et al., "Aerodynamic Focusing of Particles and Molecules in Seeded Supersonic Jets," *American Institute of Aeronautics and Astronautics, Inc.*, 1989, pp. 247-276.

Fernandez-Feria et al., "Brownian-Motion Limited Aerodynamic Focusing of Heavy Molecules," 1991, *Rarefied gas dynamics; Proceedings of the 17th International Symposium*, Aachen, Germany, Jul. 8-14, 1990, pp. 214-221.

Gormley and Kennedy, "Diffusion from a Stream Flowing Through a Cylindrical Tube," Proceedings of the Royal Irish Academy, vol. 52, Sect. A, pp. 163-169.

Jayne et al., "Development of an Aerosol Mass Spectrometer for Size and Composition Analysis of Submicron Particles," *Aerosol Science and Technology*, 2000, 33:49-70.

Johansen, "Flow through Pipe Orifices at Low Reynolds Numbers," *Proceedings of the Royal Society of London, Series A, Containing Papers of a Mathematical and Physical Character*, Jan. 1, 1930, 126(801): 231-245.

Liu et al., "Generating Particle Beams of Controlled Dimensions and Divergence: I. Theory of Particle Motion in Aerodynamic Lenses and Nozzle Expansions," *Aerosol Science and Technology*, 1995, 22:293-313.

Liu et al., "Generating Particle Beams of Controlled Dimensions and Divergence: II. Experimental Evaluation of Particle Motion in Aerodynamic Lenses and Nozzle Expansions," *Aerosol Science and Technology*, 1995, 22:314-324.

Liu et al., "Optimizing the Detection Efficiency of a Low Pressure, In-Situ Particle Monitor Using Aerodynamic Focusing Lenses," *Proceedings of Institute of Environmental Sciences*, 1996, 8 pages.

Osburn and Kammermeyer, "Gas Flow through small orifices," *Chemical Engineering Progress*, Apr. 1954, 50: 198-199.

Piseri et al., "Production and characterization of highly intense and collimated cluster beams by inertial focusing in supersonic expansions," *Review of Scientific Instruments*, May 2001, 72(5): 2261-2267.

Schreiner et al., "Focusing of Aerosols into a Particle Beam at Pressures from 10 to 150 Torr," *Aerosol Science and Technology*, 1989, 31: 373-382.

Schreiner et al., "Aerodynamics Lens System for Producing Particle Beams at Stratospheric Pressures," *American Science and Technology*, 1998, 29:50-56.

Tafreshi et al., "A Simple Nozzle Configuration for the Production of Low Divergence Supersonic Cluster Beam by Aerodynamic Focusing," *Aerosol Science and Technology*, 2002, 36: 593-606.

Tafreshi et al., "Simulation on the effect of Brownian motion on nanoparticle trajectories in a pulsed microplasma cluster source," *Journal of Nanoparticle Research*, 2002, 4: 511-524.

Tobias et al., "Real-Time Chemical Analysis of Organic Aerosols Using a Thermal Desorption Particle Beam Mass Spectrometer," *Aerosol Science and Technology*, 2000, 33:170-190.

Tuve and Sprenkle, "Orifice Discharge Coefficients for Viscous Liquids," *Instruments*, 1933, 6:201-206.

Zhang et al., "A Numerical Characterization of Particle Beam Collimation by an Aerodynamic Lens-Nozzle System: Part I. An Individual Lens or Nozzle," *Aerosol Science and Technology*, 2002, 36: 617-631.

Ziemann et al., "Particle Beam Mass Spectrometry of Submicron Particles Charged to Saturation in an Electron Beam," *Journal of Aerosol Science*, 1995, 26(5): 745-756.

De La Mora, "Drastic Improvement of the Resolution of Aerosol Size Spectrometers Via Aerodynamic Focusing: The Case of Variable-Pressure Impactors," *Chem. Eng. Comm*, 1996, 151:101-124.

Li and Ahmadi, "Dispersion and Deposition of Spherical Particles from Point Sources in a Turbulent Channel Flow," *Aerosol Science and Technology*, 1992, 16: 209-226.

Mallina et al., "Particle Growth in High-Speed Particle Beam Inlets," *J Aerosol Sci.*, 1997, 29(2): 223-238.

Zhang et al., "Numerical Characterization of Particle Beam Collimation: Part II Integrated Aerodynamic-Lens—Nozzle System," *Aerosol Science and Technology*, 2004, 38: 619-638.

Akedo et al., "Jet molding system for realization of three-dimension micro-structures," *Sensors and Actuators*, 1998, 69:106-112.

Girshick et al, "Hypersonic plasma particle deposition of nanostructures films and pattern," *Proceedings of the 14th International Symposium on Plasma Chemistry*, Prague, Aug. 2-6, 1999, 15(4): 581-606.

Rao et al, "Nanoparticle formation using a plasma expansion process," *Plasma Chemistry and Plasma Processing*, New York, Dec. 1, 1995 15(4): 581-606.

Dahneke and Flachsbart, "An aerosol beam spectrometer," *Aerosol Science*, Pergamon Press, Great Britain, 1972, 3: 345-349.

Dahneke et al, "Similarity theory for aerosol beams," *Journal of Colloid and Interface Science*, May 1982, 87(1): 167-179.

Estis et al, "Characteristics of a capillary-generated particle beam," *Journal of Colloid and Interface Science*, May, 1983, 93(1): 84-94.

Giggy and Friedlander, "Measurement of externally mixed sodium containing particles in ambient air by single particle mass spectrometry," *Atmospheric Environment*, 1989, Great Britain, 23(10): 2223-2229.

Hall and Beamon, "Secondary electron emission from beams of polystyrene latex spheres," *Journal of Applied Physics*, Dec. 1976, 47(12): 5222-5225.

Israel and Friedlander, "High-Speed beams of small particles," *Journal of Colloid and Interface Science*, 1967, 24: 330-337.

Seapan et al, "Aerosol characterization using molecular beam techniques," *Journal of Colloid and Interface Science*, May 1982, 87(1): 154-166.

Allen and Gould, "Mass spectrometric analyzer for individual aerosol particles," *Rev. Sci. Instrum.*, Jun. 1981, 52(6): 804-809.

Dahnke and Cheng, "Properties of continuum source particle beams. I. Calculation methods and results," *Journal of Aerosol Science*, 1979, Great Britain, 10:257-274.

Iordanoglou et al., "Deposition of nanostructured films by hypersonic impaction of nanoparticles," *18th Annual AAAR Conference*, Tacoma, WA, Oct. 11-15, 1999, 1 page.

Pollard and Cohen, "Electron-impact ionization time-of-flight mass spectrometer for molecular beams," *Rev. Sci. Instrum*, Jan. 1987, 58(1): 32-37.

Sinha and Friedlander, "Mass distribution of chemical species in a polydisperse aerosol: Measurement of sodium chloride in particles by mass spectrometry," *Journal of Colloid and Interface Science*, Aug. 1986, 112(2): 573-582.

Sinha et al, "Particle analysis by mass spectrometry," *Journal of Colloid and Interface Science*, May, 1982, 87(1): 140-153.

Stoffels and Lagergren, "On the real-time measurement of particles in air by direct-inlet surface-ionization mass spectrometry," *International Journal of Mass Spectrometry and Ion Physics*, 1982, Netherlands, 40: 243-254.

Rao et al., "Aerodynamic Focusing of Particles in Incompressible Jets," Apr. 9, 1992, *IBM paper*, East Fishkill, Hopewell Junction, NY, 23 pages.

Stoffels and Lagergren, "On the real-time measurement of particles in air by direct-inlet surface-ionization mass spectrometry," *International Journal of Mass Spectrometry and Ion Physics*, 1981, Amsterdam, 40: 243-254.

Sinha et al, "Particle Analysis by Mass Spectrometry," *Journal of Colloid and Interface Science*, May 1982, 87(1): 140-153.

Sinha And Friedlander, "Mass distribution of chemical species in a polydisperse aerosol: Measurement of sodium chloride in particles by mass spectrometry," *Journal of Colloid and Interface Science*, Aug, 1986, 112(2): 573-582.

Pollard and Cohen, "Electron-impact ionization time-of-flight mass spectrometer for molecular beams," *Rev. Sci. Instru.*, Jan. 1987, 58(1): 32-37.

Dahneke and Cheng, "Properties of continuum source particle beams. I. Calculation methods and results," *Journal of Aerosol Science*, Jul. 1978, vol. 10, pp. 257-274.

* cited by examiner

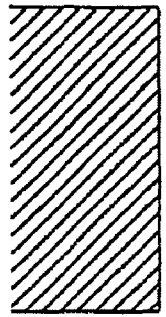 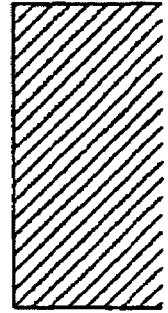 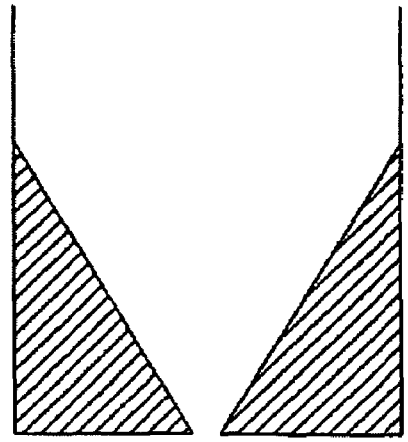
FIG. 3A.  FIG. 3B.
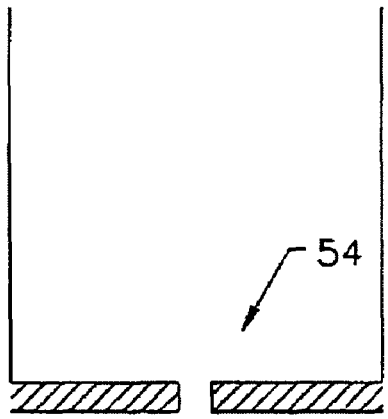 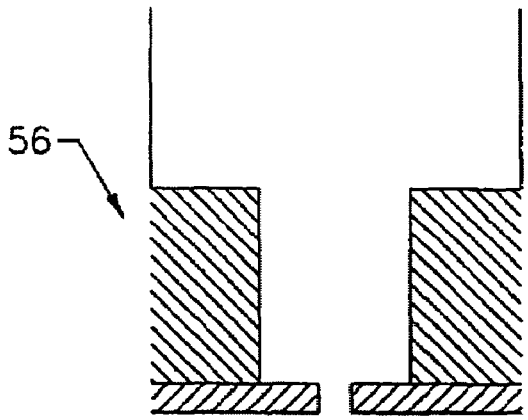
FIG. 3C.  FIG. 3D.

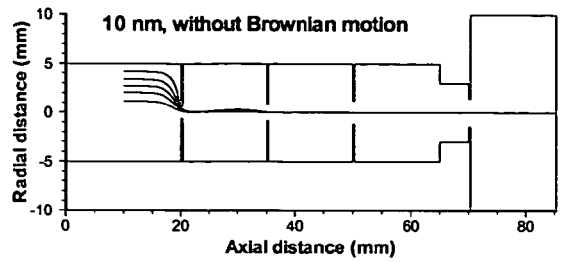
FIG. 17(g)
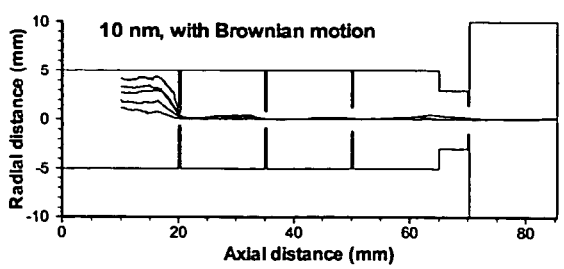
FIG. 17(h)
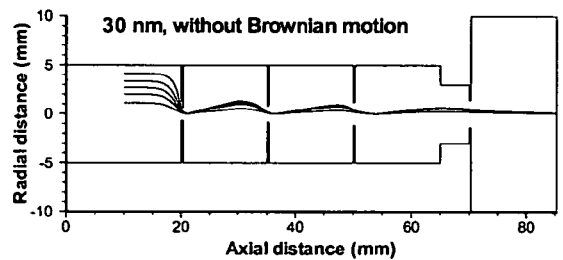
FIG. 17(i)
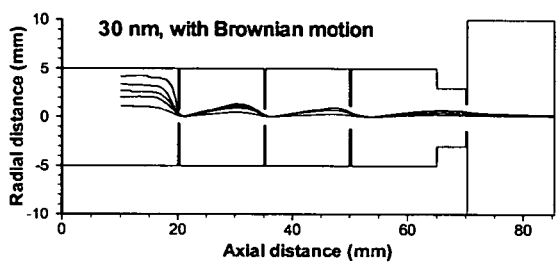
FIG. 17(j)
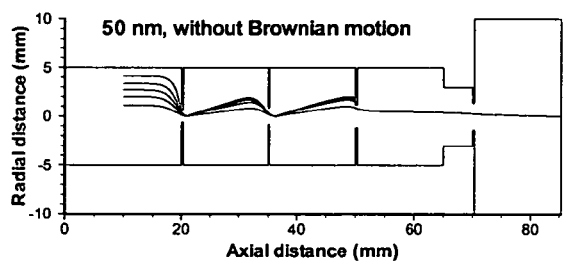
FIG. 17(k)
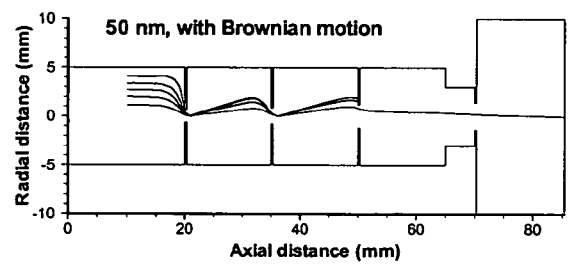
**FIG. 17(*l*)**

AERODYNAMIC FOCUSING OF NANOPARTICLE OR CLUSTER BEAMS

CROSS-REFERENCE TO RELATED APPLICATION

This application claims priority from U.S. Provisional Application 60/627,576 filed Nov. 12, 2004 and entitled "Aerodynamic Focusing of Nanoparticle or Cluster Beams," the contents of which are incorporated herein by reference.

GOVERNMENT RIGHTS

Funding for work described herein was provided in part by the federal government through National Science Foundation Grant No. DMI-0103169 and the Universität Duisburg-Essen (Germany), which may have certain rights in the invention.

TECHNICAL FIELD

This invention relates to focusing nanoparticles or clusters into a beam.

BACKGROUND

In many different areas of technology it is useful and important to obtain a focused beam of particles. A focused beam may be understood as a gas flow having a higher concentration of particles on the axis than off-axis. For example, such a particle beam can be fed in a vacuum chamber and directed as a collimated particle beam at a mass spectrometer or other apparatus that requires a well-defined input of particles for detection and/or measurement. Another example is particle deposition, where one seeks to focus the particle beam to predictably deposit a high-quality structure of particles on a substrate. Other uses for a particle beam are known in the art.

Particles smaller than 100 nm are often called nanoparticles. This definition partially overlaps with that of clusters, which is commonly used in the physics community to denote clusters of atoms or molecules in which the number of constituting elements can be counted, usually between 2 and $10^5$ at/cl (atoms per cluster). They thus represent the smaller nanoparticles. The nanoparticles or clusters can be charged. Charged clusters are known as ionized clusters. A commonly accepted method in cluster physics is the expansion of a cluster-containing gas flow through a sonic orifice or nozzle into a region of much reduced pressure. However, the pumping action necessary to remove the gas molecules also removes a major part of the clusters and leads to a cluster beam with a large divergence. The reason for this is the fact that the clusters or particles are not focused to the axis of the flow before the expansion in the low-pressure region takes place. A technique to form a more focused beam is the application of a skimmer (an orifice placed to extract only a small part of the flow, effectively reducing the beam divergence. A second skimmer can further reduce the beam divergence and is called 'collimator' (described in 'Cluster beam synthesis of nanostructured materials' by P. Milani and S, Iannotta, Springer Series in Cluster Physics, 1999).

Narrow particle beams with small divergence angles are used in many applications to enhance transport efficiency, improve measurement resolution or deposit micropatterns precisely on a substrate. For example, collimated particle beams are often used as inlets to single particle mass spectrometers to efficiently deliver particles to the analyzing region, which is typically at a pressure about 8 orders of magnitude below atmospheric. The narrow beams also help to ensure that particles pass through the most intense portion of the laser beam used to vaporize and ionize the particles (Wexler and Johnston 2001). For similar reasons, collimated beams are useful in cluster spectroscopy studies (Roth and Hospital 1994; von Issendorff and Palmer 1999) or for the analysis of heavy molecules such as proteins. Particle beams are also used in materials synthesis, whereby particles are deposited on substrates to produce ultrasmooth thin films by means of energetic cluster impact (Haberland et al. 1995a, b), to create three-dimensional microstructures (Akedo et al. 1998), or to implant large metal ions (Carroll et al. 1998).

Aerodynamic focusing is one mechanism that has been widely used to produce tightly collimated particle beams (Fernandez de la Mora and Riesco-Chueca 1988). Using the aerodynamic lenses first designed by Liu et al. (1995a, b), nearaxis particles can be focused onto a single streamline in principle. An aerodynamic lens system typically consists of three parts: a flow control orifice, focusing lenses, and an acceleration nozzle. The choked inlet orifice fixes the mass flowrate through the system and reduces pressure from ambient to the value required to achieve aerodynamic focusing. The focusing lenses are a series of orifices contained in a tube that create converging-diverging flow accelerations and decelerations, through which particles are separated from the carrier gas due to their inertia and focused into a tight particle beam. The accelerating nozzle controls the operating pressure within the lens assembly and accelerates particles to downstream destinations. Aerodynamic lenses have been widely used in particle mass spectrometers (Ziemann et al. 1995; Schreiner et al. 1998; Schreiner et al. 1999; Jayne et al. 2000; Tobias et al. 2000), for material synthesis (Girshick et al. 2000), and for microscale device fabrication (Di Fonzo et al. 2000; Gidwani 2003).

Available designs for aerodynamic lenses effectively collimate particles as small as 30 nm. However, the focusing performance degrades dramatically as particle size drops below 20 nm. The main challenges in focusing sub-20 nm particles arise from their small inertia and high diffusivity. Because of their small inertia, nanoparticles tend to follow the gas streamlines very closely and only minor focusing can be achieved. The focusing of nanoparticles is further degraded by their high diffusivities, which lead to particle loss and beam broadening.

Several studies have been reported in which aerodynamic focusing was used effectively for very small particles. In their study of aerodynamic focusing of heavy molecules, Fernandez de la Mora et al. found that although Brownian motion of the heavy molecules seriously limited the focused beam width, molecular beams with a diameter of 0.35 of the nozzle diameter could be achieved (Fernandez de la Mora et al. 1989; Fernandez-Feria et al. 1991). They also used aerodynamic lenses to increase the resolution of impactors for nanoparticles, though detailed focusing performance of the lens systems was not reported (Fernandez de la Mora 1996; de Juan 1998; Fernandez de la Mora et al. 2003). In addition, significant focusing has been achieved using a novel focusing nozzle (herein referred to as the Italian focuser) for carbon clusters as small as 1.5 nm (Piseri et al. 2001; Tafreshi et al. 2002a, b; Piseri et al. 2004). This device utilizes two sharp turns of the aerosol flow path to focus particles to the centerline of the exit nozzle. A comparison of the Italian focuser and a typical aerodynamic lens assembly with 5 lenses (Liu et al. 1995a) is given in Table 1.

TABLE 1

Comparison of the Italian focuser (Tafreshi et al. 2002a, b) and a typical aerodynamic lens assembly (Liu et al. 1995b).

|  | Carrier gas | Pressure (Pa) | Flow time (ms) | $St_o$ | Focusing range (nm) |
|---|---|---|---|---|---|
| Focuser | Helium | 1067-4000 | 3 | 0.1 | 1-6[a] |
| Lenses | Air | 267 | 100 | 0.7-1.5 | 40-250 |

Note a: It is difficult to infer the focusing size range from their papers. The cluster size range is 1~6 nm in their experiment.

The Italian focuser operates at higher pressure and with shorter particle residence time, both of which significantly reduce diffusion effects. Furthermore, this geometry has a smaller optimal Stokes number, which enables focusing very small particles onto the centerline. Compared to an aerodynamic lens system with multiple lenses, these simple sonic inlets focus a narrower particle size range, and the focusing performance has a stronger dependence on the initial radial position of particles. Note that lighter carrier gases (hydrogen or helium) were used in the above-mentioned nanoparticle (or heavy molecule) focusing experiments.

It is well known that Brownian motion is one of the major factors that limits the formation of nanoparticle beams with aerodynamic lens systems. There are several models in the literature that provide order of magnitude estimates of the particle beam width. Fernández de la Mora et al. estimated the effects of Brownian motion on beam widths downstream of a critical orifice (Fernández de la Mora et al. 1989). Fernández de la Mora further derived an asymptotic expression for diffusion-limited beam width in a periodic series of focusing lenses in the limit of Stokes number much smaller than unity (Fernández de la Mora 1996). Liu et al. developed an analytical expression for the diffusion-controlled particle beam width downstream of the accelerating nozzle assuming that all particles start from the axis with a frozen Maxwell-Boltzmann radial velocity distribution (Liu et al. 1995a, b). However, diffusion effects were neglected in most numerical simulations of particle trajectories through aerodynamic lens systems (Liu et al. 1995a, b; Zhang et al. 2004). The only work that incorporated Brownian motion in particle trajectory calculations was that by Gidwani (Gidwani 2003). Both Lagrangian and Eulerian approaches were used in that work to study particle focusing down to 10 nm. However, that lens assembly was not optimized for focusing sub-30 nm particles, and only the beam broadening inside the lenses was studied. The Lagrangian approach was followed to track particle trajectories in this work.

Existing technology can acceptably focus beams of particles of unit density as small as 30 nanometers (nm) in diameter. Some of these approaches involve the use of aerodynamic lenses, which may include a restriction disposed in the gas flow, the restriction having an aperture of a specific size. At smaller diameters, however, generally towards 20 nm, the focusing performance decreases. At sufficiently small particle sizes, there is currently no known aerodynamic lens that can provide acceptable focusing.

SUMMARY

The present invention provides improvements relating to aerodynamic lenses and apparatus including one or more such lenses. Particularly, embodiments of the invention relate to focusing nanoparticles or clusters to the center of an axisymmetric gas flow, thereby allowing the formation of a tightly collimated beam of clusters or nanoparticles. The aerodynamic lenses optimized for nanoparticles allow cluster-laden gases to be expanded in a low-pressure or vacuum chamber with a high transmission efficiency and resulting in more tightly collimated cluster beams.

Embodiments may provide acceptable focusing of spherical particles of unit density in the 2-30 nm diameter range. This range will be extended towards even smaller particle diameters for particles having larger than unit density. Non-spherical particles can also be focused, but to a lesser degree due to defocusing by the lift force. The invention also provides a procedure for designing such lenses and corresponding apparatus. Such a procedure can be implemented such that it can be performed by a computer. Accordingly, a computer program product that is embodied in an information carrier, including any computer-readable medium, can include instructions for performing one or more steps of any method or procedure described herein.

Embodiments of a method to design an aerodynamic lens can be applied in manufacturing a variety of aerodynamic lenses having an effect, when placed before the expansion in the low-pressure chamber, of enhancing the transmission efficiency (defined as the probability for particles of a given size to pass the transition region from the high into the low pressure region) of nanoparticles and clusters. Such method embodiments may furthermore result in a more collimated beam (i.e., a beam with smaller divergence), thus further increasing the transmission efficiency when passing through a skimmer or collimator.

Mass spectrometers according to the invention may be used in the area of proteomics, where it is useful to produce a concentrated stream of particles (e.g., proteins) at an inlet to a machine. Such inventive embodiment may increase the concentration of the particles, which improves the efficiency of sampling.

The flow of the aerosol gas can take place at an optimal Stokes number if those conditions provide a continuum, subsonic and laminar flow. In other situations, a suboptimal Stokes number may be used.

In a first general aspect, an apparatus for shaping an aerosol beam having particles suspended in a gas comprises an aerodynamic lens having an aperture therethrough, wherein a size of the aperture and an operating pressure of the aerodynamic lens are selected so that the aerodynamic lens focuses particles having a size as small as about 3 nm.

Embodiments of the apparatus may include any or all of the following features. The aerodynamic lens may operate at an optimal Stokes number. The optimal Stokes number may be about 0.6. The aerodynamic lens may operate at a suboptimal Stokes number. The operating pressure at which the aerodynamic lens focuses the particles may be selected such that it exists above a Mach limit pressure and above a Knudsen limit pressure. The aperture, the operating pressure and the particle diameter may satisfy a relationship for focusing the particles. The relationship may provide that the operating pressure can be calculated given the mass flow rate of the gas, the particle properties, the Stokes number and the aperture dimensions. The relationship may provide that the operating pressure is proportional to:

$$\left[ \frac{1}{(1+\frac{\pi\alpha}{8})\sqrt{2\pi\gamma^3}} \frac{\dot{m}\rho_p d_p c^3}{d_f^3 St_o} \right]^{\frac{1}{2}}$$

wherein
$\alpha$ = a momentum accommodation coefficient;
$\gamma$ = a ratio of specific heats of the gas;
$\dot{m}$ = a mass flowrate of the gas;
$\rho_p$ = a particle material density;
$d_p$ = the particle diameter;
$c$ = speed of sound in the gas at a temperature upstream of the aerodynamic lens;
$d_f$ = the aperture size; and
$St_o$ = Stokes number for the particles.

The aerodynamic lens may be positioned in a tube between spacers having an diameter that is at least several times the aperture size. The apparatus may further comprise several aerodynamic lenses, each lens configured to focus particles having a specific size. Apertures of the several aerodynamic lenses may have different sizes. The several aerodynamic lenses may operate at optimal Stokes numbers. The several aerodynamic lenses operate at suboptimal Stokes numbers. The suboptimal Stokes numbers may be selected such that operating pressures of the several aerodynamic lenses exist above a Mach limit pressure and above a Knudsen limit pressure. The diameter may be at most about 5 nm. The diameter may be at most about 1 nm. The apparatus may comprise at least one selected from the group consisting of: an apparatus for performing chemical analysis, a mass spectrometry apparatus, a particle deposition apparatus, a cluster beam apparatus, and combinations thereof. When the apparatus comprises the cluster beam apparatus, the aerodynamic lens may reduce particle losses between a high-pressure cluster-producing surrounding and a low-pressure cluster-beam surrounding. The aperture may be circular or rectangular. The apparatus may comprise at least two aerodynamic lenses.

In a second general aspect, a method of designing an apparatus including an aerodynamic lens disposed in a tube for shaping an aerosol beam comprises obtaining a relationship between i) a size of particles suspended in the aerosol beam, ii) an operating pressure for the aerodynamic lens, and iii) a size of an aperture in the aerodynamic lens. The method comprises selecting, using the relationship, the operating pressure to provide subsonic continuum flow of the aerosol beam through the aerodynamic lens. The method comprises selecting the aperture size using the relationship.

Embodiments of the method may include any or all of the following features. The aerodynamic lens may be configured to operate at an optimal Stokes number. The aerodynamic lens may be configured to operate at a suboptimal Stokes number. The method may further comprise selecting the operating pressure such that it exists above a Mach limit pressure and above a Knudsen limit pressure. The relationship may provide that the operating pressure can be calculated given the mass flow rate of the gas, the particle properties, the Stokes number and the aperture dimensions. The relationship may provide that the operating pressure is proportional to:

$$\left[\frac{1}{(1+\frac{\pi\alpha}{8})\sqrt{2\pi\gamma^3}}\frac{\dot{m}\rho_p d_p c^3}{d_f^3 St_o}\right]^{\frac{1}{2}}$$

wherein
$\alpha$=a momentum accommodation coefficient;
$\gamma$=a ratio of specific heats of the gas;
$\dot{m}$=a mass flowrate of the gas;
$\rho_p$=a particle material density;
$d_p$=the particle diameter;
c=speed of sound in the gas at a temperature upstream of the aerodynamic lens;
$d_f$=the aperture size; and
$St_o$=Stokes number for the particles.

The method may further comprise selecting an inner diameter for spacers in the tube, the inner diameter being at least several times the aperture size. The method may comprise reducing a spacer length to reduce particle residence time and particle diffusion. The apparatus may be designed to include several aerodynamic lenses, each lens configured to focus particles having a specific size. Apertures of the several aerodynamic lenses may have different sizes. The several aerodynamic lenses may operate at optimal Stokes numbers. The several aerodynamic lenses may operate at suboptimal Stokes numbers. The method may further comprise selecting the suboptimal Stokes numbers such that operating pressures of the several aerodynamic lenses exist above a Mach limit pressure and above a Knudsen limit pressure. Selecting operating pressures and aperture sizes for the several aerodynamic lenses may comprise an iterative procedure. The iterative procedure may comprise a) estimating a discharge coefficient and an expansion factor based on a Reynolds number, a mass flow rate and an operating pressure upstream of the first aerodynamic lens of the several aerodynamic lenses, b) calculating a pressure drop and the aperture size using the mass flow rate, the discharge coefficient and the expansion factor, and c) repeating steps a) and b) until convergence. Particle diffusion may be taken into account in selecting the operating pressure. Selecting the operating pressure may comprise identifying a maximum operating pressure at which a rate of particle diffusion is acceptable. Selecting the operating pressure or aperture size may comprise selecting a lighter carrier gas or a mixture of different carrier gases, with at least one of the different carrier gases being lighter than an initial carrier gas.

In a third general aspect, a method of designing an apparatus including an aerodynamic lens disposed in a tube for shaping an aerosol beam having particles suspended in a gas comprises selecting a particle size range, a particle density for the particles, and an aerosol mass flow rate. The method comprises calculating a maximum operating pressure for the apparatus that provides a laminar continuum flow of the gas. The method comprises calculating a size for an aperture in the aerodynamic lens using the maximum operating pressure. The method comprises selecting an inner diameter and lengths of spacers for the apparatus.

Embodiments of the method may include any or all of the following features. Calculating the maximum operating pressure may comprise a step selected from the group consisting of: solving equations for the laminar continuum flow and for particle focusing, identifying an intersection of graphs in a diagram, and combinations thereof. The step may provide a calculated pressure and calculating the maximum operating pressure may comprise reducing the calculated pressure by a predefined amount. The method may further comprise selecting a lighter carrier gas or a mixture of different carrier gases, with at least one of the different carrier gases being lighter than an initial carrier gas, and performing the steps of calculating the maximum operating pressure and the aperture size for the lighter carrier gas or the mixture of different carrier gases. Calculating the maximum operating pressure may comprise selecting a lower Stokes number for the particles upon determining that the maximum operating pressure does not provide continuum flow of the gas. The method may further comprise evaluating, upon determining that the maximum operating pressure does not provide continuum flow of the gas, whether using several aerodynamic lenses in the apparatus can provide the laminar continuum flow of the gas. The method may further comprise decreasing the mass flow rate, upon determining that flow through the aerodynamic lens is not laminar, and thereafter calculating a new maximum operating pressure and lens dimension using the decreased mass flow rate. The method may further comprise estimating particle diffusion losses and particle beam width for the laminar continuum flow.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 3A-3D schematically shows cross-sectional views of exemplary prefocusing and primary focusing elements utilized by the FIG. 1 apparatus.

FIGS. 17a-l show particle trajectories through a nanoparticle lens system with and without Brownian motion.

Like reference numerals in the various drawings indicate like elements.

DETAILED DESCRIPTION

Figure 1:
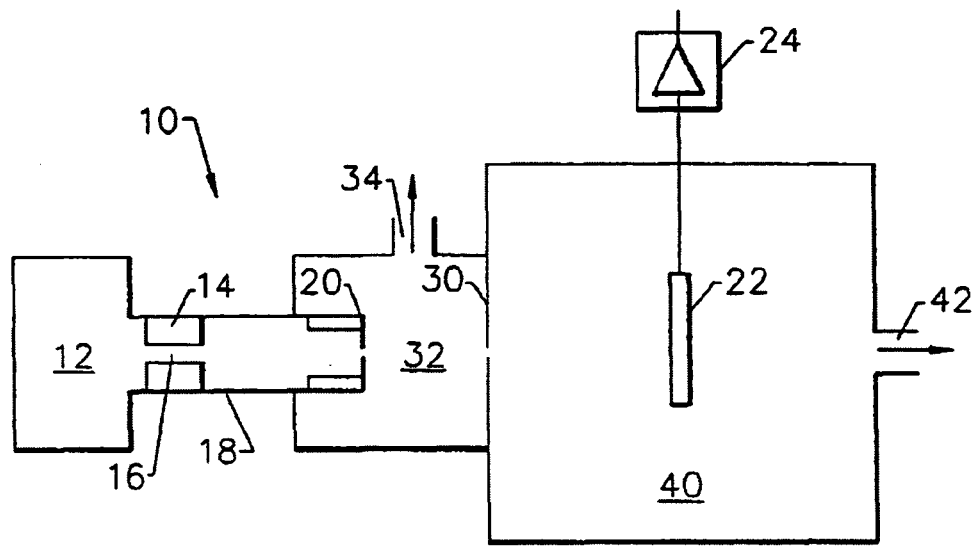
FIG. 1 schematically shows an apparatus for focusing a nanoparticle beam or a cluster.

An apparatus for focusing a nanoparticle beam or a cluster may include one or more aerodynamic lenses, an accelerating nozzle, spacers and a tube. Such an apparatus can be a chemical-analysis apparatus, a mass spectrometer apparatus, a particle deposition apparatus, or a cluster beam apparatus, to name a few examples.

Referring now to FIG. 1, an apparatus for focusing a nanoparticle or cluster beam is illustrated. The aerosol beam shaping apparatus 10 receives aerosol from an aerosol beam source 12 in which particles are mixed with a gas. The particles are relatively heavy in comparison to the lighter gas. The aerosol beam source 12 may be a sample of particles suspended in a gas, such as that present during a microelectronic device processing step, in which the number and size, if desired, of the particles present are to be determined.

The apparatus 10 here includes a receiving device 40 that receives nanoparticles or clusters that have been focused. That is, the focusing of the particles or clusters is used to provide them in a concentrated way to the receiving device for further processing. A variety of receiving devices may be provided, in which the focused particles or clusters are used for one or more purposes. To name a few examples, the receiving device 40 may comprise an apparatus for performing chemical analysis, a mass spectrometry apparatus, a particle deposition apparatus, a cluster beam apparatus, or combinations thereof. The example of the receiving device 40 shown in FIG. 1 includes a detection means 22 that will be described below with reference to FIG. 4.

The apparatus 10 includes a focusing means 14 for receiving the aerosol beam. The focusing means 14 may be a constriction and particularly a capillary tube 50, a converging conical nozzle 52, a thin plate 54 having an orifice defined therethrough; or either a converging conical nozzle or a capillary tube with a thin plate 56 having an orifice therein disposed downstream of and adjacent thereto as illustrated in FIGS. 3A-3D. As shown in FIG. 1, the orifice 16 in the focusing means 14 defines the aerosol beam because the received aerosol is confined to passing through the orifice 16.

Figure 2:
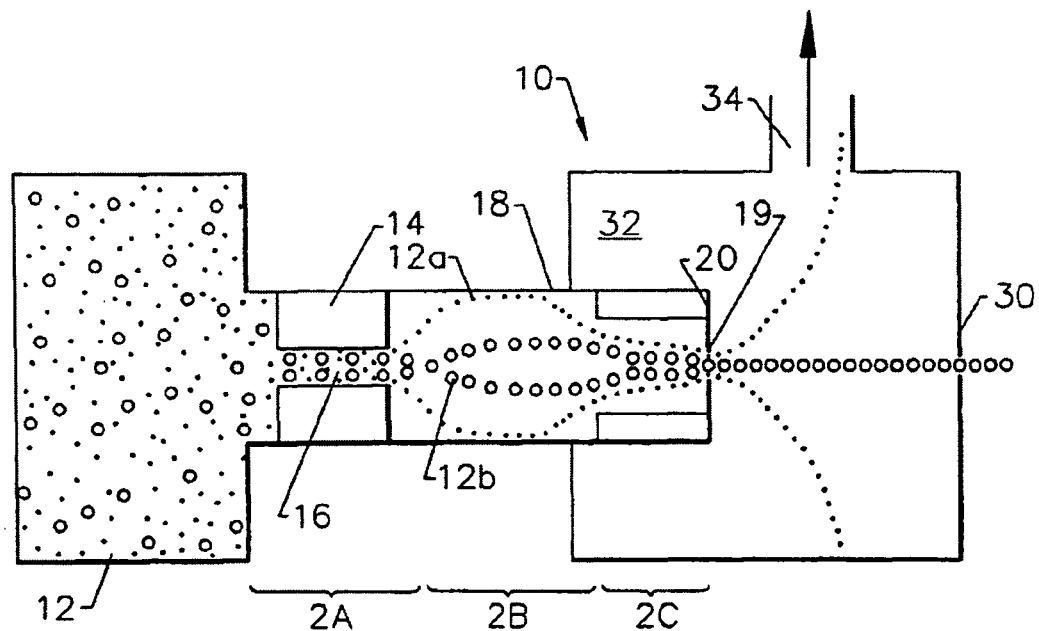
FIG. 2 schematically shows a cross-sectional view of the paths of particles and gas in the FIG. 1 apparatus.

As illustrated by FIG. 2, the focusing means 14 produces a relatively rapid lateral expansion of the gas 12a emerging therefrom while the particles 12b initially converge to a focal point prior to expanding laterally relatively slowly. This preferential lateral expansion of the aerosol, shown in region 2A of FIG. 2, is due to the larger inertia of the particles 12b in comparison to the gas 12a. The mass of the particles 12b is substantially greater than that of the gas 12a so as to give the particles 12b a substantially greater inertia than that of the gas 12a. With larger inertia, the particles 12b diverge less from the longitudinal axis of propagation established by the focusing means 14 in comparison to the lighter gas 12a which has less inertia and thus diverges more rapidly from the longitudinal axis.

The aerosol beam shaping apparatus 10 includes a tube 18 or other lateral confining means for laterally confining the rapidly expanding gas emerging from the focusing means 14 as shown in region 2B of FIG. 2. The focusing means 14 is preferably disposed within the tube 18 such that the orifice 16 of the focusing means 14 has a substantially smaller diameter than the inner diameter of the tube 18.

As shown in region 2C of FIG. 2, additional focusing means 20 converges the gas 12a, which has been laterally confined by the tube 18, back upon the particles 12b to further narrow the cross-sectional area of the particle beam. The additional focusing means 20 may be disposed within the tube 18 downstream of and spaced apart from the focusing means 14 such that the laterally confined gas 12a is forced, by the interface of the tube 18 and the additional focusing means 20, back upon the longitudinal beam of particles 12b. The focusing means 14 is the primary focusing element in the aerodynamic lens system. The additional focusing means 20, in contrast, is not a primary focusing element and may be designed to minimize beam expansion. The additional focusing means 20 has an orifice 19 therethrough having a diameter substantially smaller than the inner diameter of the tube 18. As illustrated in FIGS. 3A-3D, the additional focusing means 20 may be a constriction such as a capillary tube 50; a converging conical nozzle 52; a thin plate 54 having an orifice therein; or either a converging conical nozzle or a capillary tube with a thin plate 56 having an orifice therein disposed downstream of and adjacent thereto.

The aerosol beam shaping apparatus 10 may produce a particle beam for use in detecting the number and size of particles in the aerosol beam source 12. To detect the number or presence of particles in the thus-formed particle beam, the apparatus 10 is used in conjunction with the detection means 22 positioned downstream of the additional focusing means 20 as illustrated in FIGS. 1 and 4.

Various particle detection methods may be utilized. The particles may be electrically charged and may thereafter be detected with the detection means 22. The detection means 22 may be an electron multiplier, a scintillation type detector or a Faraday cup detector, including a Faraday cup detector comprising a metal plate or collector cup to which an electrometer 24 is connected. The detection means 22 measures the electric current associated with the charged particles impacting the metal plate. A thin layer of electrically conducting vacuum grease may be applied to the metal plate of the Faraday cup detector in order to prevent particles from bouncing off the metal plate and not being detected.

Figure 4:
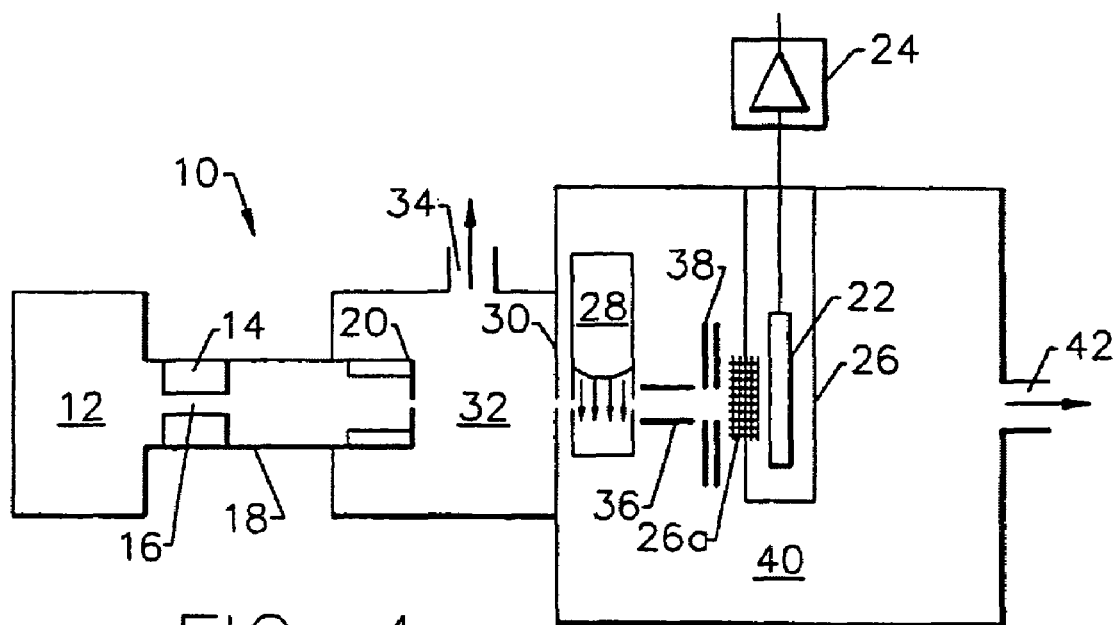
FIG. 4 schematically shows a cross-sectional view of the FIG. 1 apparatus including detection means.

As shown in FIG. 4, the detection means 22 may be disposed within a grounded metal housing 26 to shield the detection means 22 from electric fields and stray electrons. A first face of the metal housing 26, oriented upstream to receive the particle beam, includes a grounded wire mesh grid 26a for allowing particles to pass therethrough in order to be detected.

In order to electrically excite the particles prior to their detection, a particle excitation means 28 may be positioned downstream of the additional focusing means 20 as shown in FIG. 4. The particle excitation means may excite the particles photoelectrically or electrically. The particle excitation means 28 may produce a substantially planar sheet of electrons oriented substantially parallel to the longitudinal axis of the narrowed particle beam so as to intersect the particle beam and impart an electrical charge to the particles. By utilizing a planar sheet of electrons, the particle excitation means 28 significantly increases the number of interactions between particles and electrons in comparison to a cylindrical electron stream. By increasing the number of interactions between particles and electrons, the number of charged particles and thus the charging efficiency of the particle beam is increased.

In addition, electron and light ion deflection means 38 may be associated with and downstream of the particle excitations means 28. Electrons and light ions, such as electrically-charged gas molecules, may be deflected with a magnetic field. An electric field may be established by the electron and light ion deflection means 38. In particular, the electron and light ion deflection means 38 may be a pair of electron deflection plates having an electric field established therebetween. The electron deflection plates are positioned such that the charged particle beam flows therebetween and stray electrons, not associated with a particle, as well as light ions are deflected or removed from the particle beam. The deflected electrons and light ions are therefore not subsequently detected.

Referring again to FIGS. 1 and 4, a particle separation means 30, preferably a skimmer, may be interposed between the additional focusing means 20 and the particle beam excitation means 28. The skimmer 30 may be a thin plate having an orifice therein and may be disposed at a first end of a chamber 32 with the additional focusing means 20 located at a second end of the chamber 32. The skimmer 30 is spaced apart from the additional focusing means 20 to allow the particles and gas emerging from the additional focusing means 20 to preferentially expand once again such that the gas expands laterally relatively rapidly while the particles initially converge to a focal point prior to expanding laterally relatively slowly. The particle separation means 30 may be located at the particles' focal point to increase the particles' transmission efficiency therethrough. The chamber 32 also has a vacuum port 34 such that the rapidly laterally expanding gas is drawn through the vacuum port 34 while the slowly expanding particle beam passes through the orifice defined by the skimmer 30.

If the relative masses of the particles, in addition to the number of particles is to be determined, particle deflection means 36, such as a pair of particle deflection plates, may be interposed between the particle excitation means 28 and the detection means 22. The particle deflection plates have different electric potentials applied thereto to generate an electric field therebetween. The particle deflection plates are positioned such that the charged particle beam passes therebetween. The particles are deflected by the electrical force resulting from the interaction of the electric field established by the particle deflection plates and the electric charge associated with the particle. By measuring the amount of deflection of the particles at varying electric field strengths, the particles' relative masses may be calculated therefrom.

In FIG. 4, the receiving device 40 comprises a detection chamber 40. Here, the detection chamber 40 houses the particle excitation means 28; the particle deflection means 36, if any; the electron deflection means 38; and the detection means 22. The detection chamber 40 has a vacuum port 42 such that a pressure differential may be established between the relatively lower pressure of the detection chamber 40 and the relatively higher pressure of the aerosol beam source 12. The pressure differential draws the aerosol beam from the aerosol beam source 12 to the detection chamber 40.

The various examples of the present description refer to particles, nanoparticles and clusters. These terms can be used by scientists in any of several disciplines, and there may also be other terms used only in certain fields that have a more specific meaning. For example, an aerosol scientist may use "nanoparticle" as an all-encompassing term, while a physicist or physical chemist refers to molecular "clusters" and a biochemist talks about large "molecules." While these entities may have sizes that are of the same order of magnitude, they have very different structures and properties and the various terms are therefore not synonymous.

In this description, the term "particle" is used in a general sense and refers to all of the types of matter or material that can be focused using embodiments of the invention. That is, the term does not only cover that which a physicist may call a "particle" but rather entities from a range of scientific fields. This means that the present description is directed toward focusing that can be performed on a variety of matters and materials including, but not limited to, nanoparticles, clusters and molecules.

The size or sizes of the particles to be focused is also discussed throughout this description. In some cases, a range of sizes is discussed. The size of a spherical particle usually means the diameter of the particle. The size of nonspherical particles may be determined using its mass and by approximating the particle with a unit density sphere. For example, embodiments of the invention can be used in proteomics research to focus large molecules such as proteins. They may have molecular weights in the 100,000 to 1,000,000 Dalton range. When "aerosolized," such molecules are considered to have the sizes 6.8 nm and 14.7 nm, respectively, based on the assumption that they become unit density spheres in the aerosol. In some situations, the size may mean a maximum dimension that a nonspherical particle is known (or believed) to have. There will now be described examples of approaches for designing an aerodynamic lens or an apparatus including such a lens. The following exemplary description targets the design of aerodynamic lens systems to focus nanoparticles. We first describe a viscous flow model that estimates the flowrate and pressure drop through orifices with reasonable accuracy. We then determine the minimum particle size that can be focused exactly onto the axis with a single lens provided diffusion is absent. Next we describe a systematic procedure that minimizes the size of particles that can be focused, which minimizes effects of diffusion as well. We conclude with an example problem that illustrates the use of these design guidelines for an aerodynamic lens to focus 5 nm unit density spherical particles using helium as the carrier gas, and proves the validity of the design procedure by comparison with more detailed trajectory simulations based on computational fluid dynamics (CFD) calculations.

The task of aerodynamic lens design is to optimize the operating parameters (flowrate, pressure and carrier gas) and lens geometry (orifice size, number of lenses, inner diameter and length of spacers between lenses) to obtain best lens performance (maximum particle focusing, minimum particle loss, minimum volumetric pumping capacity for a given mass flowrate, etc.).

As shown in previous studies, particle focusing by means of an aerodynamic lens made of a thin plate orifice is mainly determined by the Stokes number (St) (Liu et al. 1995 a, b). In the free molecule regime, the Stokes number can be defined using Epstein's mobility model (Liu et al. 1996; Friedlander 2000) as:

$$St = \frac{1}{\left(1 + \frac{\pi\alpha}{8}\right)\sqrt{2\pi\gamma^3}} \frac{\dot{m}\rho_p d_p c^3}{p_1^2 d_f^3}, \quad [1]$$

where $\alpha$ is the momentum accommodation coefficient, $\gamma$ is the specific heat ratio of the carrier gas, $\dot{m}$ is the mass flowrate, $\rho_p$ is the particle material density, $d_p$ is particle mass diameter (Tammet 1995), $$c = \sqrt{\frac{\gamma R T_1}{M}}$$

is the speed of sound in the carrier gas at the temperature ($T_1$) upstream of the aerodynamic lens, R is the universal gas constant (8.314 J/mol K), M is the molecular weight of the carrier gas, $p_1$ is the static pressure upstream of the orifice (note that the flow velocity upstream of the orifice is typically low, and the static pressure is close to the stagnation pressure), and $d_f$ is the aperture diameter of the aerodynamic lens.

Various researchers have proposed corrections to the Epstein mobility model when particles are a few nanometers in diameter (Tammet 1995; Loscertales 2000; Fernández de la Mora et al. 2003; Li and Wang 2003a, b). Considering these corrections, the Stokes number of a neutral particle can be expressed as $$St = \frac{1}{\left(1 + \frac{\pi\alpha(d_p)}{8}\right)\sqrt{2\pi\gamma^3}} \frac{\dot{m}\rho_p d_p c^3}{p_1^2 d_f^3} \left(\frac{d_p}{d_p + d}\right)^2 \sqrt{1 + \frac{m_g}{m_p}}, \quad [2]$$

where d is an effective diameter of the gas molecule when it collides with a particle, $m_p$ is the particle mass, and $m_g$ is the mass of the gas molecular. There are three differences between Equations (2) and (1). First, $\alpha$ is a function of particle diameter instead of a constant. Its value changes from 0 for elastic collision (gas-molecule) to ~0.9 for inelastic collision (gas-particle). For neutral particles, the term $$\left(1 + \frac{\pi\alpha}{8}\right)$$

is equivalent to s in Equation 16 of Tammet (1995). Second, the term $$\left(\frac{d_p}{d_p + d}\right)^2$$

is a correction that accounts for the difference between particle mobility diameter and mass diameter, where $d=d_g+2h$ and $d_g$ is gas molecule diameter inferred from gas viscosity, and $2h$ is an "extra distance" estimated to be 0.23 nm (Tammet 1995). Finally, the term $$\sqrt{1+\frac{m_g}{m_p}}$$

is a correction for the reduced mass of gas molecule and particle. For reasons that will be explained later, we neglected the three corrections mentioned above in this description, i.e., we use Equation (1) as the formula for the Stokes number.

The particle Stokes number determines the extent to which particle trajectories deviate from flow streamlines. Following Liu et al.'s notation, we define the particle stream contraction factor ($\eta$) as the ratio of the terminal and initial radial locations of the particle passing through the lens. Note that $\eta$ is approximately independent of the initial radial position for particles close to the lens axis (Liu et al. 1995a). Only the near-axis contraction factor is considered when deriving the design guidelines. The relationship between $\eta$ and St is summarized as follows: $|\eta| \approx 1$ for St<<1 (not focused), $|\eta|<1$ for St$\approx$1 (focused), and $|\eta|>1$ for St>>1 (defocused). The optimum Stokes number $St_o$, for which near-axis trajectories cross the axis at infinity ($|\eta|=0$), is of order of 1 for a thin plate lens, and varies somewhat with the lens geometry and flow pattern (Liu et al. 1995a; Liu et al. 1996; Zhang et al. 2002). Several studies have shown that $St_o$ decreases with increasing half-angle of the nozzle (Fernández de la Mora and Riesco-Chueca 1988; Fernández de la Mora et al. 1989). Therefore, a nozzle with half-angle of 90° (thin plate orifice) or even larger favours focusing of small particles compared to those with smaller angles (conical nozzle, capillary). We use a thin plate orifice as the aerodynamic lens in this work due to its simple geometry and relatively small $St_o$.

The orifice diameter $d_f$ required to focus particles of diameter $d_p$ can be determined by rearranging Equation (1):

$$d_f = \left\{ \frac{1}{(1+\frac{\pi\alpha}{8})\sqrt{2\pi\gamma^3}} \frac{\dot{m}\rho_p d_p c^3}{p_1^2 St} \right\}^{\frac{1}{3}}. \quad [3]$$

Usually, the optimum focusing Stokes number $St_o$ is used in Equation (3) to design a lens. However, we will show later that using a Stokes number smaller than $St_o$ sometimes offers advantages when designing lenses for nanoparticles. On the other hand, a system designed to work with a larger Stokes number, such as 1.2, may also work but may be somewhat inferior.

An aerodynamic lens system may include a series of lenses, each optimized to focus particles of a specified size. This approach enables focusing a wide range of particle sizes. Ideally, with a sufficient number of lenses, spherical particles can be confined arbitrarily closely to the centerline if Brownian motion and turbulence are negligible.

As shown in Equation (3), the upstream pressure $p_1$ is an important parameter in aerodynamic lens design. Therefore, the pressure drop across an orifice needs to be estimated accurately when designing a system with multiple lenses. Liu et al. (1996) used a quasi-one-dimensional isentropic flow model to estimate the pressure drop across the orifice. They pointed out that this flow model might underestimate the pressure drop, especially at low Reynolds numbers. In fact, aerodynamic lenses typically operate at Reynolds numbers lower than 100 where viscous effects have to be included. In this work, the following equation is used to model flow through an orifice (Bean 1971):

$$\dot{m} = A_f \frac{C_d Y}{\sqrt{1-\beta^4}} \sqrt{2\rho_1(p_1-p_2)} = A_f \frac{C_d Y}{\sqrt{1-\beta^4}} p_1 \sqrt{\frac{2M}{RT_1} \frac{\Delta p}{p_1}}, \quad [4]$$

where $A_f$ is the cross section area of the orifice, $C_d$ is the discharge coefficient defined as the ratio of the actual viscous-incompressible flowrate to theoretical inviscid-incompressible flowrate through an orifice, Y is an expansion factor which accounts for the effect of compressibility on the flowrate calculated according to incompressible flow, $\beta$ is the ratio of orifice to tube diameters, $\rho_1$ is the density upstream the orifice, $p_2$ is the fully recovered pressure downstream of the orifice, and $\Delta p = p_1 - p_2$ is the pressure drop across the orifice.

Figure 5:
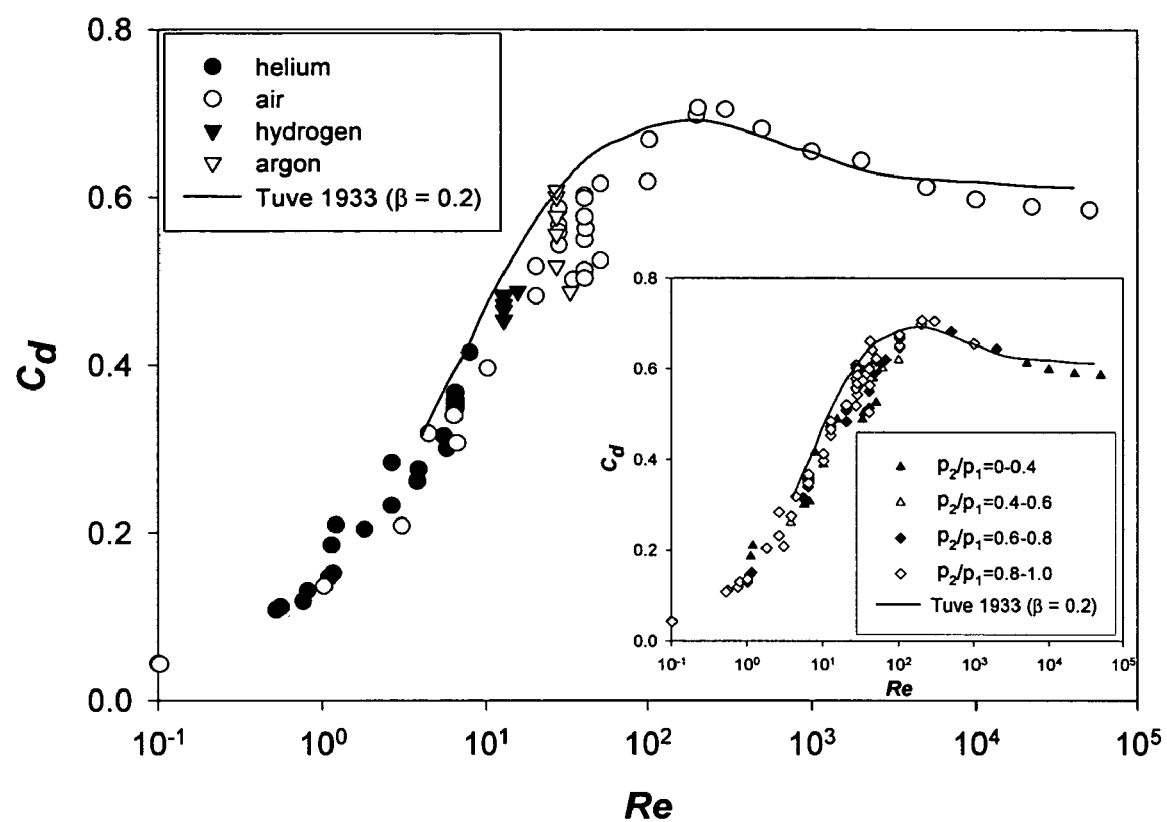
FIG. 5 shows discharge coefficient as a function of Reynolds number for flow through a thin plate orifice. The data points are obtained from CFD simulations ($0.1 < \beta < 0.5$) and the solid curve is a fit of experimental data by Tuve and Sprenkle (1933). The insert shows that after correction for the compressibility, Cd simulated from gas flow over a wide range of pressure ratios follows the same trend as the data from liquid experiments.

The discharge coefficient of a thin plate orifice is ideally a function of flow Reynolds number and the diameter ratio ($\beta$) of the orifice and tube containing the orifice (Tuve and Sprenkle 1933). Here the Reynolds number is defined as $$Re = \frac{\rho_1 u d_f}{\mu} = \frac{4\dot{m}}{\pi \mu d_f}, \quad [5]$$

where $$u = \frac{4\dot{m}}{\pi \rho_1 d_f^2}$$

is the average flow velocity at the orifice based on upstream temperature and pressure conditions and $\mu$ is the gas viscosity. When $\beta<0.5$, $C_d$ is relatively insensitive to $\beta$ and is only a strong function of the Reynolds number. At high Reynolds numbers (Re>5000), $C_d$ is approximately constant. At Reynolds number lower than 5000, $C_d$ rises and then falls rapidly as the Reynolds number is decreased (Johansen 1930). In the creeping flow regime (Re<10), $C_d$ is proportional to $Re^{0.5}$ (Osburn and Kammermeyer 1954). We have carried out simulations of different gases through orifices to obtain the Reynolds number dependent discharge coefficient using the commercial CFD software FLUENT (version 6.1.22). The discharge coefficients obtained from these simulations are summarized in FIG. 5. $\beta$ varied from 0.1 to 0.5 in these simulations. Also shown in FIG. 5 are measurements with incompressible liquids (Tuve and Sprenkle 1933). Note that after using the expansion factor Y to account for the gas compressibility, our simulation shows that the discharge coefficient for different carrier gases falls on the same trend line as those by Tuve and Sprenkle (1933) over a wide range of pressure ratios (see the insert). The observed variability in simulated values of $C_d$ arises from variabilities in $\beta$ and, to a lesser extent, in Mach number. The simulated discharge coefficient can be fitted to the following equation:

$$C_d = \begin{cases} 0.1373Re^{0.5} & (Re < 12) \\ 1.118 - 0.8873 \times \text{Ln}(Re) + 0.3953 \times [\text{Ln}(Re)]^2 - \\ 0.07081 \times [\text{Ln}(Re)]^3 + 0.005551 \times [\text{Ln}(Re)]^4 - \\ 0.0001581 \times [\text{Ln}(Re)]^5 & (12 \le Re < 5000) \\ 0.59 & (Re \ge 5000) \end{cases} \quad [6]$$

For subsonic flow through a thin plate orifice, an empirical equation for the expansion factor was derived from experiments (Bean 1971):

$$Y = 1 - (0.410 + 0.350\beta^4)x/\gamma, \quad [7]$$

where x is given by:

$$x = \frac{p_1 - p_2}{p_1}. \quad [8]$$

With this flow model, the errors in pressure drop or mass flowrate are within ±10% for all cases we tested.

When designing a system of multiple lenses with given $\dot{m}$ and $p_1$, one may first use Equation (3) to calculate the lens diameter. Then Equation (4) is used iteratively to calculate the pressure drop across the lens. This procedure continues to design the remaining lenses. A software program may be developed for designing and evaluating aerodynamic lens systems.

The design of aerodynamic lens systems to focus nanoparticles may follow the general procedure described above. However, the low inertia and high diffusivity of nanoparticles introduce major challenges in focusing them aerodynamically. In order to achieve Stokes numbers of order 1, it is necessary to either use very small orifices or very low pressures (see Equation (1)). Small orifices either limit flowrate to very low values or result in large Reynolds numbers, and they can be difficult to machine and can clog easily. Operating at very low pressures requires a large pumping capacity and enhances the detrimental effects of diffusion. In this section, we will first find the minimum particle size that can be focused to the axis with a single orifice and the corresponding operating conditions when diffusion effects are neglected. Then we will discuss guidelines to minimize nanoparticle diffusion.

To find the minimum particle size that can be focused to the axis with a single aerodynamic lens, we rewrite the Stokes number in the following format (Fernández de la Mora et al. 1989):

$$St = \frac{FeMa^2}{Re} \approx FeMaKn\sqrt{\frac{1}{2\pi\gamma}}, \quad [9]$$

with $Fe = \dfrac{\gamma m_p \rho_1 D}{m_g \mu}$ (Fenn number), [10]

$Ma = \dfrac{u}{c} = \dfrac{u}{\sqrt{\dfrac{\gamma k T_1}{m_g}}}$ (flow Mach number), [11]

$Kn = \dfrac{2\lambda_1}{d_f}$ (flow Knudsen number), [12]

$$D = kT_1 B = \frac{3}{2\sqrt{2\pi}}\left(1 + \frac{\pi\alpha}{8}\right)^{-1}\frac{1}{d_p^2}\frac{(kT_1)^{\frac{3}{2}}}{p_1}\frac{1}{\sqrt{m_g}}. \quad [13]$$

where D is the particle diffusion coefficient (Friedlander 2000), k is the Boltzmann constant ($1.38 \times 10^{-23}$ J/K), $\lambda_1$ is the mean free path of the gas molecules upstream of the orifice, and B is the particle mobility. Re, Kn, and Ma are all based on fluid properties upstream of the orifice. It can be shown that in the free molecular regime, Fe is independent of pressure and is only weakly dependent on temperature. Fe depends only on gas and particle properties, and is approximately proportional to $\rho_p d_p$ (Fernández de la Mora et al. 1990). On the other hand, the term $$\frac{Ma^2}{Re}$$

or Ma Kn depends solely on the flow condition and gas properties.

In this description, the flow through aerodynamic lenses is constrained to be continuum and subsonic. Presumably, if flow through lenses were supersonic, then a shock wave would form between lenses, which would likely adversely affect focusing. If the flow were in the free molecular regime, the fluid dynamic simulations and the viscous flow model are invalid and no reliable design is possible. Furthermore the concept of particle Stokes number becomes invalid because of insufficient collisions in the gas. The particle focusing behaviour in these regimes remains to be studied in more detail. The continuum and subsonic constraints impose maximum limits on Knudsen number (Kn*) and Mach number (Ma*). We take Kn≦Kn*=0.1 in this description. Note that Kn*=0.1 is somewhat arbitrary, and one can easily adjust the result in this section if the true Kn* were not 0.1. We will show later in this description that uncertainty about the exact value of the Kn* is not very important, because nanoparticle lenses are typically designed to operate as far as possible from the Kn limit. Ma* depends on the Reynolds number, as is discussed below.

We define a critical condition under which the flow at the vena contracta changes from subsonic to sonic (Ward-Smith 1979). From Equation (4), we obtain the critical mass flowrate $\dot{m}_c$ through an orifice $$\dot{m}_c = A_f \frac{C_d Y_c}{\sqrt{1-\beta^4}} p_1 \sqrt{\frac{2M}{RT_1} x_c}, \quad [14]$$

where $Y_c$ is defined by Equation (7), with $$x = x_c = \frac{\Delta p_c}{p_1} \approx 1 - \left(\frac{2}{\gamma+1}\right)^{\frac{\gamma}{\gamma-1}}. \quad [15]$$

The Mach number of the critical flow can then be obtained from Equations (11) and (14)

$$Ma^* = Y_c C_d \sqrt{\frac{2x_c}{\gamma}}, \quad [16]$$

where the term $\beta^4$ is neglected because $\beta$ is typically less than 0.5. Note that Ma* is a function of Reynolds number through $C_d$ as given in Equation (6).

Kn, Ma and Re are related to each other so that one can write the following expression $$Re^* = \frac{Ma^*}{Kn^*}\sqrt{2\pi\gamma} = \frac{2Y_c C_d}{Kn^*}\sqrt{\pi x_c}.$$ [17]

For a fixed Kn* value (0.1 as chosen in this work), Ma* and Re* are fixed for a given carrier gas and the values can be found iteratively using Equations (6), (7), (15) and (17). By imposing the limits of Ma≦Ma*, Kn≦Kn* and rearranging Equation (9), we obtain $$Fe \geq \frac{St_o}{Ma^* Kn^*}\sqrt{2\pi\gamma}.$$ [18]

Substituting in the definition of Fenn number (Equation (10)), we have $$\rho_p d_p \geq \frac{8St_o}{Ma^* Kn^*}\left(1 + \frac{\pi\alpha}{8}\right)\mu\sqrt{\frac{m_g}{kT_1\gamma}}.$$ [18]

Figure 6:
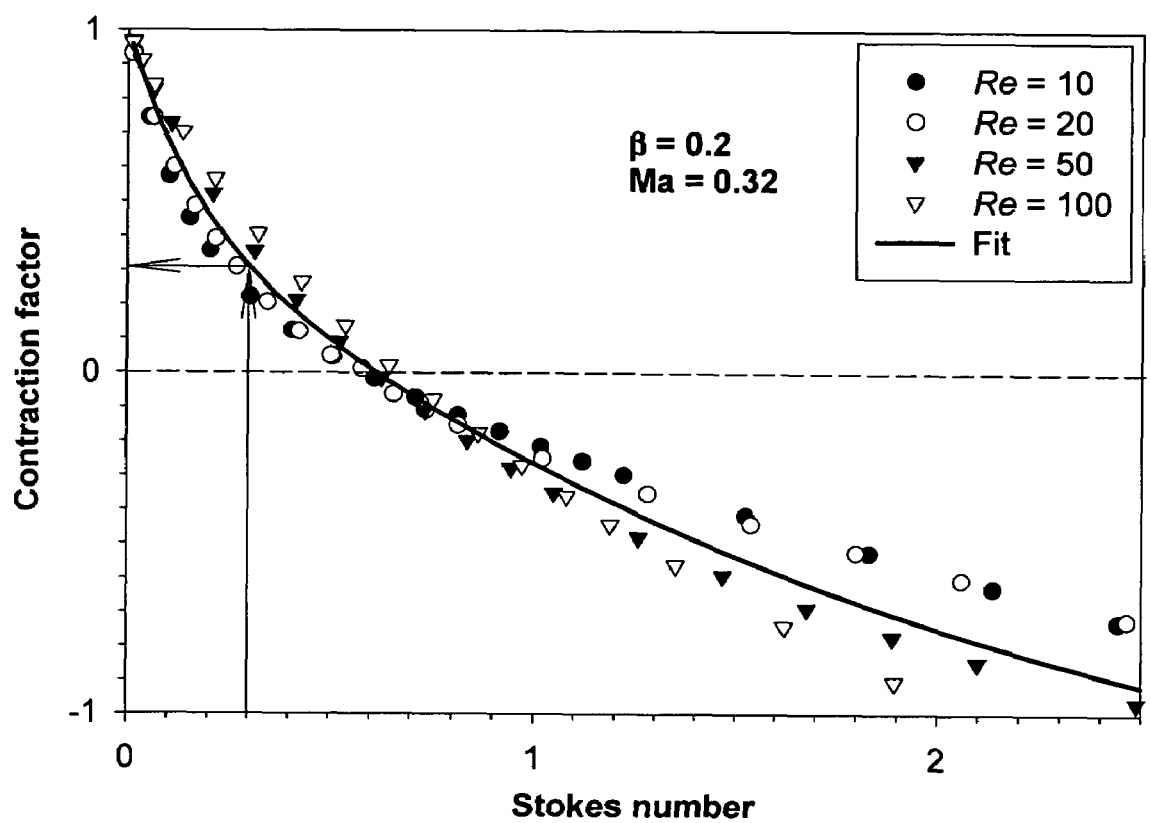
FIG. 6 shows near-axis particle contraction factors through a single lens with $\beta=0.2$, Ma=0.32, and Re=10-100.

To obtain $St_o$ at flow close to the critical conditions, we numerically calculated the near-axis particle contraction factor as a function of Stokes number through an aerodynamic lens with β=0.2, Ma=0.32, and Re=10–100. The result is shown in FIG. 6. Note that the contraction factor is not a strong function of Reynolds number in the Stokes number range of 0-1. Previous work also showed that the contraction factor in the range of –1<η<1 is not a strong function of Ma (Liu et al. 1995a). Therefore, a best fit of the simulated data (solid curve) is a good representation of the contraction factor for nanoparticle lenses. FIG. 6 shows the optimum Stokes number $St_o \approx 0.6$. Note that for critical flow with fixed Kn*' the minimum value of $\rho_p d_p$ depends only on properties of the carrier gas. Typically, lighter carrier gases (smaller $m_g$) allow focusing of smaller particles. Minimum focusing sizes ($d_{p1}$) of particles with a density of 1 g/cm³ in several carrier gases are given in Table 2. Also listed are the corresponding lens diameter and operating pressure when the flowrate is 0.1 standard liters per minute (slm).

Note b: Properties values are for reference temperature $T_r$=296.15 K and pressure $p_r$=101325 Pa.

If we include the three correction factors in Equation (2), the minimum size ($d_{p2}$) can be calculated using the following equation $$\frac{\rho_p d_p^3}{(d+d_p)^2} \geq \frac{8St_o}{Ma_{limit} Kn_{limit}}\left(1 + \frac{\pi\alpha(d_p)}{8}\right)\mu\sqrt{\frac{m_g}{kT_1\gamma}}\sqrt{\frac{m_p}{m_g+m_p}}.$$ [20]

The values of $d_{p2}$ for various gases are also shown in Table 2. Note that the difference between $d_{p1}$ and $d_{p2}$ is not very significant. Furthermore, the empirical relations of $\alpha(d_p)$ and d in Equation (20) were fitted from limited experimental data in air (Tammet 1995). It is not yet known whether these values are valid for other carrier gases. More experimental data are required to validate these relations. Therefore, we have confined our analysis to the Stokes number expression (Equation (1)) derived from the classic mobility model of Epstein.

Since the two most important parameters to be determined when designing an aerodynamic lens are the orifice diameter and operating pressure, we will next determine the lens operating pressure range as a function of orifice diameter for a given mass flowrate and particle properties.

From Equation (14), we can obtain the Mach limit of pressure $p_{Ma}$ $$p_1 > p_{Ma} = \frac{\dot{m}_c}{C_d Y_c A_f} / \sqrt{\frac{2M}{RT_1}x_c}.$$ [21]

When the operating pressure is lower than $p_{Ma}$, the volumetric flowrate is higher at the given mass flowrate $\dot{m}_c$, and the flow velocity at the throat will be sonic. Therefore, the operating pressure ($p_1$) of an aerodynamic lens must be higher than $p_{Ma}$ so that the flow is subsonic. Note that $p_{Ma}$ is proportional to $Q_{STP}M^{0.5}$, where $Q_{STP}$ is the volumetric flowrate at standard conditions.

Substituting Sutherland's law $$\lambda_1 = \lambda_r \frac{T_1}{T_r}\frac{p_r}{p_1}\frac{1+S/T_r}{1+S/T_1}$$ [22]

into the condition of continuum flow Kn<Kn*, we have

TABLE 2

Gas properties, minimum focusing diameter, and focusing conditions when the flowrate is 0.1 slm for five different carrier gases at 296.15 K.

| Gas | M (g/mol) | $\mu_r$ (×10⁻⁵ Pa·s)[b] | $\lambda_r$ (nm)[b] | γ | $d_{p1}$ (nm) | $d_{p2}$ (nm) | $d_f$ (mm) | $p_1$ (Pa) |
|---|---|---|---|---|---|---|---|---|
| $H_2$ | 2.016 | 0.8861 | 124.0 | 1.4 | 1.6 | 2.2 | 2.6 | 96.7 |
| He | 4.003 | 1.9711 | 194.3 | 1.63 | 4.5 | 5.2 | 2.1 | 187.2 |
| Air | 28.966 | 1.8347 | 67.4 | 1.4 | 12.4 | 13.2 | 18.0 | 7.6 |
| Ar | 39.948 | 2.2480 | 70.3 | 1.668 | 15.9 | 16.7 | 18.1 | 7.9 |
| $CO_2$ | 44.010 | 1.4812 | 43.8 | 1.310 | 12.9 | 13.9 | 35.5 | 7.1 |

$$p_1 > p_{Kn} = \frac{2}{d_f Kn^*} \lambda_r \frac{T_1}{T_r} p_r \frac{1+S/T_r}{1+S/T_1}, \quad [23]$$

where $\lambda_r$ is the gas molecule mean free path at the reference conditions $T_r$ and $p_r$ (see Table 2), S is the Sutherland constant and $p_{Kn}$ is the minimum pressure for continuum flow. Note that $p_{Kn}$ depends on the carrier gas through $\lambda_r$.

The operating pressure required to focus particles of given size and density can be obtained from Equation (3)

$$p_{focusing} = p_1 = \left[ \frac{1}{(1+\frac{\pi\alpha}{8})\sqrt{2\pi\gamma^3}} \frac{\dot{m}\rho_p d_p c^3}{d_f^3 St_o} \right]^{\frac{1}{2}}. \quad [24]$$

It can be shown that $p_{focusing}$ is proportional to $Q_{STP}^{0.5} M^{-0.25}$.

Figure 7A:
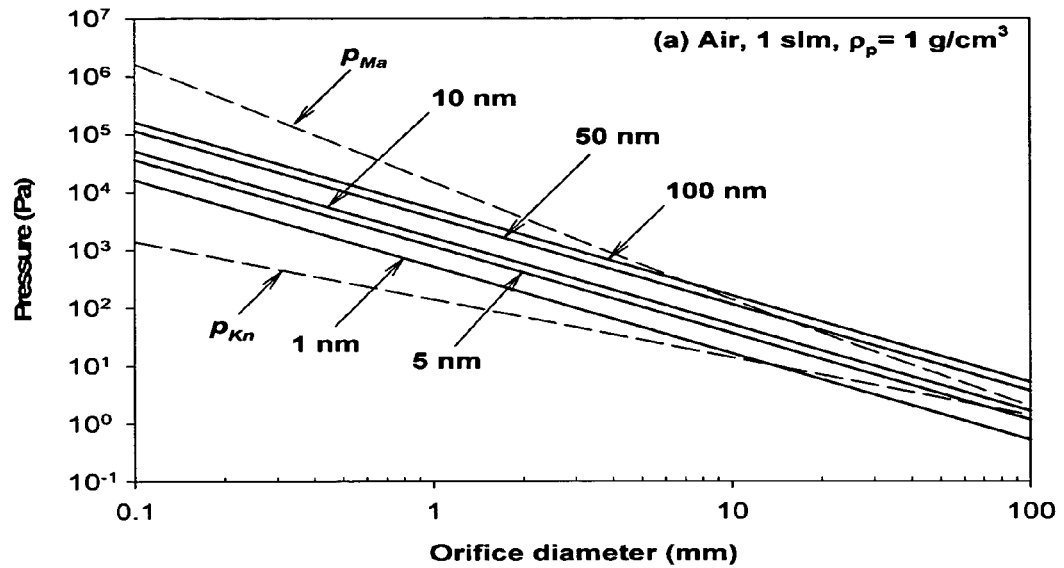
FIG. 7 shows the Mach number and Knudsen number pressure limits and focusing pressure for spherical unit density particles of different sizes as functions of orifice size at air flowrates of (a) 1 slm and (b) 0.1 slm. Particles of each size can be optimally focused when the corresponding $p_{focusing}$ is larger than $p_{Ma}$ and $p_{Kn}$ (see Equations (21), (23) and (24)).
Figure 7B:
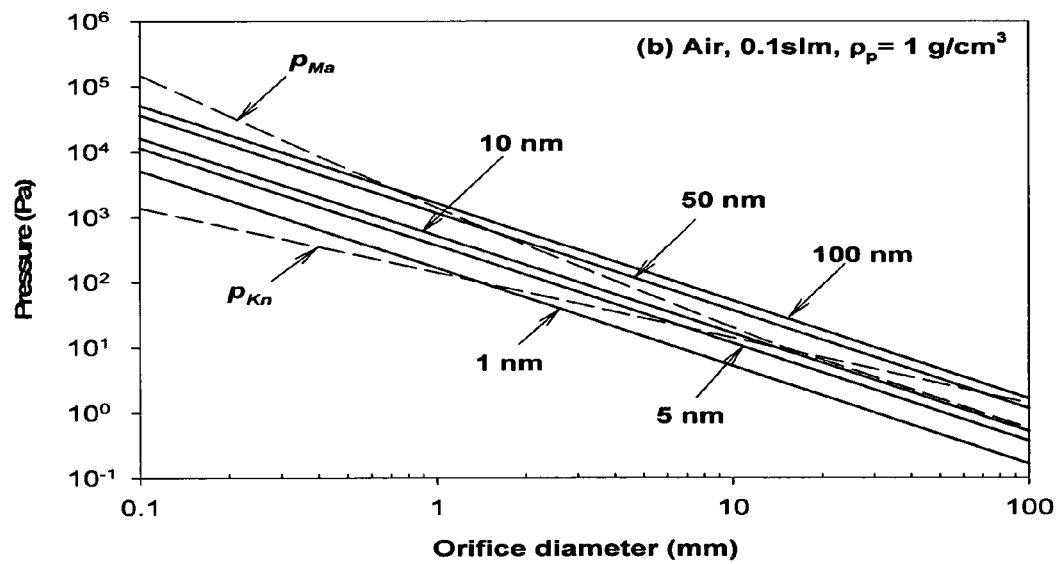
Figure 8A:
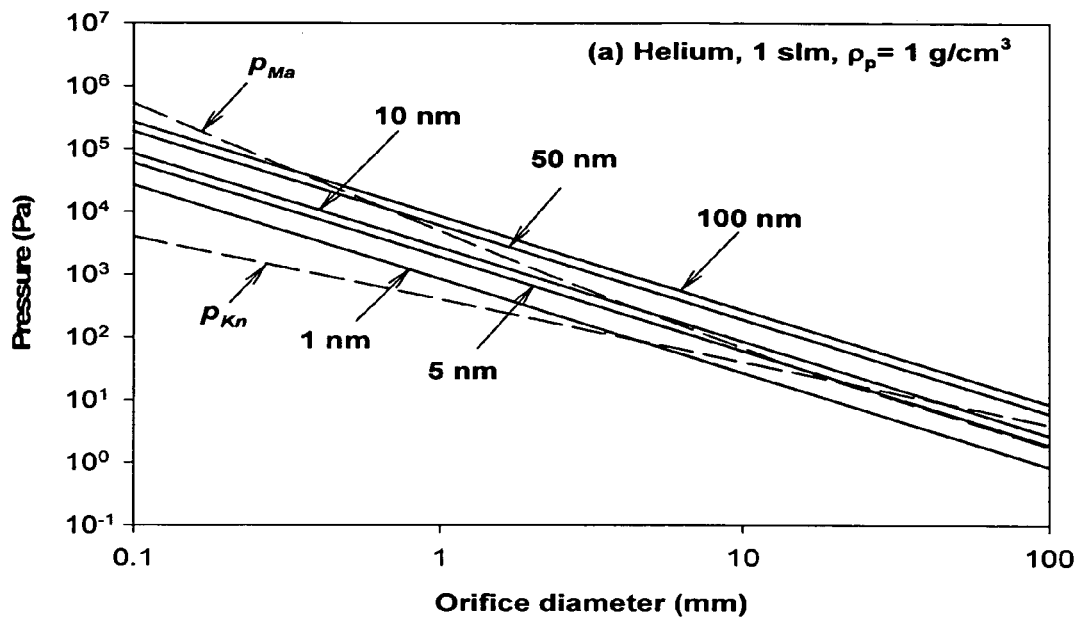
FIG. 8 shows the Mach number and Knudsen number pressure limits and focusing pressure for unit density particles of different sizes as functions of orifice size at helium flowrates of (a) 1 slm and (b) 0.1 slm.
Figure 8B:
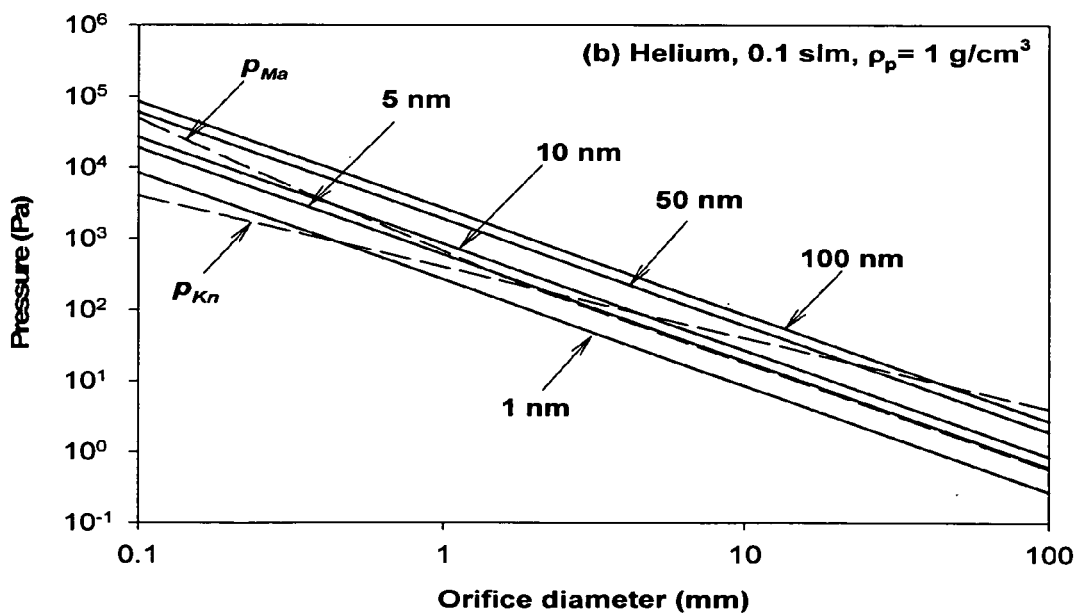

FIG. 7 shows $p_{Ma}$, $p_{Kn}$ and the required $p_{focusing}$ to focus particles of different sizes in air as functions of the orifice size. The same information is shown in FIG. 8 for helium. The available operating pressure range for focusing is where $p_{focusing}$ is larger than both $p_{Ma}$ and $p_{Kn}$. Note that for a given carrier gas, smaller mass flowrates expand the available pressure range as predicted by Equations (21) and (24). However, the Knudsen number limit $p_{Kn}$ becomes more important at lower flowrates. The point where $p_{Ma}$, $p_{Kn}$ and $p_{focusing}$ curves intersect determines the minimum size that can be focused and is identified as $dp_1$ in Table 2.

Figure 9:
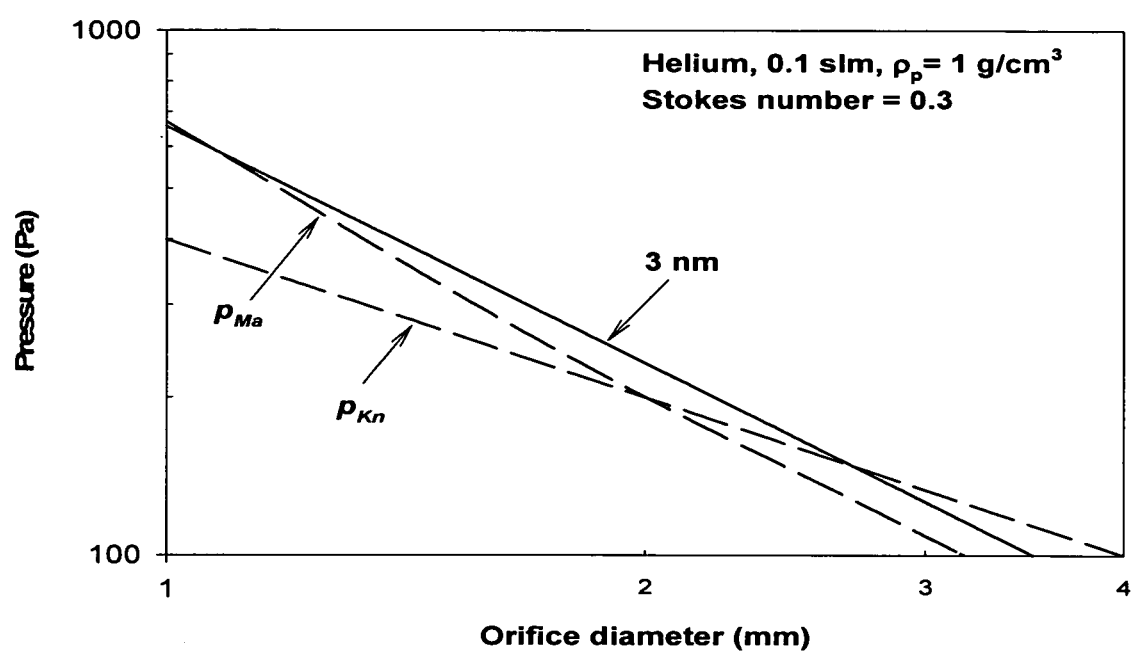
FIG. 9 shows the Mach number and Knudsen number pressure limits, and the operating pressure range for focusing 3 nm particles at St=0.3.

To focus particles smaller than $d_{p1}$ in Table 2, we can use multiple lenses operating at Stokes numbers smaller than the optimum Stokes number. It is evident in Equation (24) that $p_{focusing}$ is larger when a Stokes number smaller than $St_o$ is used. As shown in FIG. 9, when the lens operates at St=0.3, there is a wide range of operating pressures larger than $p_{Ma}$ and $p_{Kn}$ for sub-optimally focusing 3 nm particles. FIG. 6 shows that a single lens will create a contraction factor of about 0.31 for near-axis particles with St=0.3. When n such lenses are used in series, the total contraction factor will be $(0.31)^n$. Thus four such lenses can create a particle beam that is about 100 times tighter than the initial beam size if diffusion is neglected. The design and evaluation of a lens system focusing 3 nm particles will be discussed below.

Particle diffusion was not included in the preceding analysis. In this section, we will consider particle loss and particle beam broadening due to diffusion, and derive a maximum pressure under which particles are focused with minimum diffusion while flow is continuum and subsonic.

The high diffusivity of nanoparticles leads to two adverse effects: particle diffusional loss and particle beam broadening. Particle diffusional loss is most important before particles are focused away from the walls towards the lens axis. However, diffusional broadening is more important when particles are tightly focused due to the high gradient of the particle concentration between the particle beam the surrounding carrier gas. Fernández de la Mora derived an expression for an asymptotic diffusion-limited particle beam width inside aerodynamic lenses (Fernández de la Mora 1996). Liu et al. (1995a) developed an analytical expression for the effects of diffusion on the spread of particle beams downstream of the accelerating nozzle. They assumed that all particles were focused to the axis at the nozzle exit, and the radial speed could be described by the Maxwell-Boltzmann distribution. They obtained the following Brownian limit expression for the diameter of the particle beam that encloses 90% of the total particle number flux:

$$d_{B,Brown} = 3.04 \sqrt{\frac{2kT_{pF}}{m_p}} \frac{L}{U_p}, \quad [25]$$

where $T_{pF}$ is the particle frozen temperature in the nozzle expansion, $d_{B,Brown}$ is width of the particle beam which encloses 90% of the particle number flux, L is the distance from the nozzle to where the particle beam width is measured, and $U_p$ is the mean axial speed of particles in the vacuum downstream of the nozzle. To obtain tight particle beams, it is important to limit the diffusion loss and broadening both inside and after lenses.

Equation (1) shows that the Stokes numbers required to focus nanoparticles can be achieved by reducing the operating pressure. Unfortunately, as is shown in Equation (13), particle diffusion coefficients increase when the pressure is decreased. The key to designing aerodynamic lenses for nanoparticles is to find a pressure that is sufficiently low to achieve focusing, but sufficiently large to avoid excessive effects of diffusion.

We can roughly estimate nanoparticle losses due to diffusion inside the aerodynamic lenses by calculating the penetration through tubes with fully developed laminar flow using the Gormley-Kennedy equation (Gormley and Kennedy 1949). This equation will overestimate particle losses since the aerodynamic lenses will focus particles closer to the axis and away from walls but it serves here as a guideline in the design procedure. The penetration is highest for the smallest values of the dimensionless deposition parameter ξ, defined by:

$$\xi = \frac{DL}{Q}, \quad [26]$$

where L is length of the spacer between two lenses, and can be estimated as $$L = N d_f \quad [27]$$

N is usually between 10 and 50, depending on flow Reynolds number. Q is the volumetric flowrate through the tube given by $$Q = \frac{\dot{m}}{\rho_g} = \frac{\dot{m}kT_1}{p_1 m_g}. \quad [28]$$

Substituting Equations (3), (13), (27), and (28) into Equation (26) leads to $$\xi = \left(\frac{1}{p_1 \dot{m}}\right)^{2/3} \frac{3kT_1 N}{2\pi} \left(\frac{\pi \rho_p}{4 St_0 d_p^5 (1+\frac{\pi\alpha}{8})^4}\right)^{1/3} \propto \left(\frac{1}{p_1 \dot{m}}\right)^{2/3} \frac{T_1 N}{St_0^{1/3}} \left(\frac{\rho_p}{d_p^5}\right)^{1/3} \quad [29]$$

Note that ξ is larger for lower $p_1$. Therefore, diffusional losses decrease as pressure increases.

Higher operating pressure is also preferred for lowering the pumping capacity. The volumetric flowrate Q removed by the pump at the lens upstream flow condition (related to the pumping speed) is $$Q = Q_{STP} \frac{p_{STP}}{p_1} \frac{T_1}{T_{STP}} \qquad [30]$$

where $Q_{STP}$ is the volumetric flowrate at standard temperature $T_{STP}$ and pressure $p_{STP}$ conditions. It is clear that the pumping speed Q is lower with higher $p_1$.

Both the requirements of minimizing the pumping capacity and diffusional losses lead to the same conclusion: lenses should be designed to operate at the highest possible operating pressure.

The maximum possible pressure is the intersection of the curve of $p_{Ma}$ and the curve of focusing pressure for each particle size in FIGS. 7, 8 and 9. For example, $p_{max} \approx 580$ Pa at $d_f \approx 1.1$ mm in FIG. 9. The exact value of $p_{max}$ can be obtained by rearranging Equations (21) and (24) to eliminate the orifice diameter, $$p_{max} = \qquad [31]$$
$$M^{-\frac{5}{2}} \frac{RT_{STP}}{Q_{STP}P_{STP}} (2RTx_c)^{\frac{3}{2}} \left[ \frac{1}{\left(1+\frac{\pi\alpha}{8}\right)\sqrt{2\pi\gamma^3}} \frac{\rho_p d_p}{St_o} \right]^2 \left( \frac{\pi}{4} Y_c C_d \gamma \right)^3.$$

Note that term $p_{max}Q_{STP}$, which defines the lens operating condition, is proportional to $$M^{-\frac{5}{2}} (\rho_p d_p)^2$$

for a given Reynolds number. It is clear that smaller M yields larger $p_{max}Q_{STP}$ (i.e., higher operating pressure and therefore less particle diffusion, or larger volumetric flowrate at standard conditions). It is interesting to note that when a choked nozzle is used, small particle velocities ($U_p$ in Equation (25)) are higher for lighter carrier gases due to their higher speed of sound. Therefore, using lighter carrier gases has the additional benefit of reducing particle beam broadening downstream of the accelerating nozzle. This confirms that a lighter carrier gas is preferred for focusing smaller particles. We should point out that $p_{max}$ determined above is typically larger than the intersection of $p_{kn}$ and $p_{focusing}$ in FIGS. 7, 8 and 9. Therefore, the lenses are designed to operate at a Knudsen number smaller than Kn* as much as possible. The uncertainty in the exact value of Kn* is thus not very important.

We should note that maximizing the operating pressure is only applicable to focusing small particles. At higher pressures, the orifice diameter to focus a certain size would decrease, which in turn would increase Reynolds number. When the flow becomes unstable or turbulent, focusing is destroyed. When focusing particles<30 nm, Reynolds numbers are much smaller than 100. Therefore, it is safe to maximize pressure. In order to focus large particles, where diffusion is not a concern, appropriate intermediate pressures need to be chosen according to pumping capacity, flow Reynolds number and orifice size.

Figure 10:
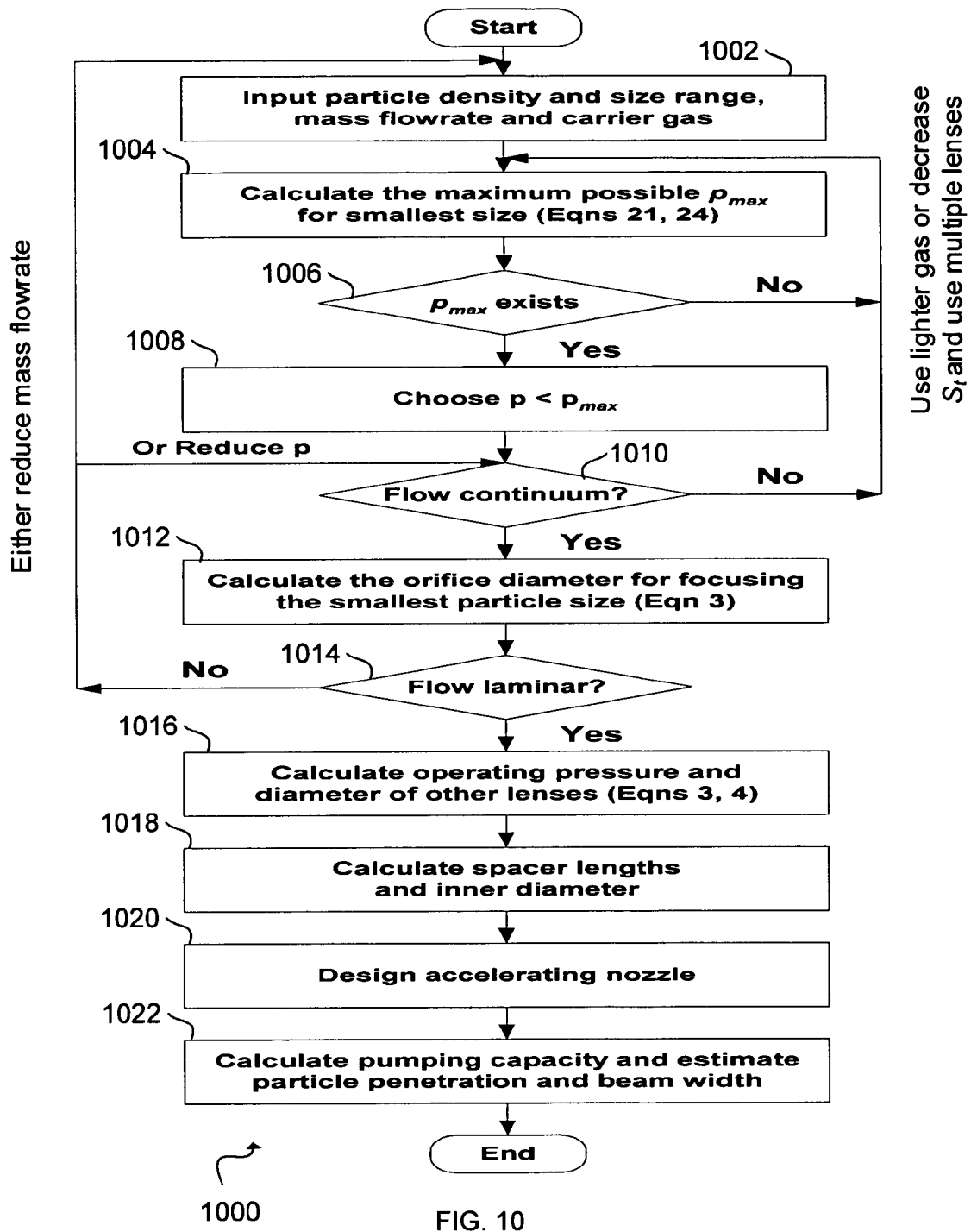
FIG. 10 shows a flow chart for designing aerodynamic lens systems for nanoparticles.

A flow chart for an exemplary process 1000 of designing aerodynamic lens systems for nanoparticles is shown in FIG. 10. Define the particle density and size range, the carrier gas, and the mass flowrate through the system in step 1002. Calculate the maximum possible operating pressure ($p_{max}$) for focusing the smallest particle in the size range using Equations (21) and (24) in step 1004. This can also be read approximately from a figure similar to FIG. 7 or 8 (the intersection of $p_{Ma}$ and $p_{focusing}$ for that particle size). In some cases, it is determined in step 1006 that a value for $p_{max}$ does not exist (e.g. 1 nm in FIG. 8(b)). Then a lighter carrier gas or multiple lenses operating at sub-optimal Stokes numbers should be used, as indicated in the return to step 1004. There may be used a lighter carrier gas or a mixture of different carrier gases, with at least one of the different carrier gases is lighter than the original carrier gas. This approach may be useful in targeting a particular size of particles for focusing, and may reduce or minimize residence time for the particles. Since the flow through a lens needs to be subsonic, we choose a focusing pressure smaller than $p_{max}$ (e.g. $p_{max} \times 0.9$) in step 1008. Meanwhile, this operating pressure should be larger than $p_{Kn}$ (Equation (23)) to satisfy the continuum flow condition in step 1010. Calculate the orifice diameter for focusing the smallest particle size in the size range using Equation (3) in step 1012. Flow through the orifice should be laminar, and this is determined in step 1014. Otherwise, one needs to reduce either the mass flowrate or the operating pressure, as indicated in the returns to step 1002 and step 1010, respectively. However, the criterion of Re for laminar flow through a thin plate orifice is not yet known. Several experiments indicated that the flow becomes unstable around Re=70 (Eichler et al. 1998; Gómez-Moreno et al. 2002). We suggest limiting Re<120 before further work determines the critical Re. After designing this last orifice, one can use Equations (3) and (4) to calculate the operating pressure and diameter of the preceding orifices for focusing successively larger particles in step 1016. Calculate the lengths and inner diameter of spacers in step 1018. The optimum Stokes number is a function of the ratio of the orifice diameter and the spacer inner diameter (β) (Liu et al. 1995a; Zhang et al. 2002). However, this dependence is weak when β≦0.25. Therefore, we suggest setting the spacer inner diameter equal to 4 times or larger than the orifice diameter. The spacers should be long enough so that the orifice jet flow reattaches to the spacer inner wall before reaching the next lens (Liu et al. 1995b). The length can be 10 to 50 times of the upstream orifice diameter depending on the orifice Reynolds number. Design the accelerating nozzle with low divergence angles as was described by Liu et al. (1995b) in step 1020. In step 1022, calculate the required pumping capacity and estimate the particle transport efficiency with Gormley-Kennedy equation, and the width of particle beam using FIG. 6.

According to the procedure described above, we designed a single aerodynamic lens to focus 5 nm particles with density of 1 g/cm³ using helium as the carrier gas. The aerosol flowrate was 0.1 slm. From Equations (21) and (24), we obtained the maximum possible operating pressure of 338 Pa. We chose the operating pressure to be 338×0.9=304.2 Pa, which yields a lens diameter of 1.562 mm from Equation (24). The spacer inner diameter was chosen to be about 5 times of the orifice diameter (8 mm), and the spacer lengths to be 20 mm. With this design, Re=12.3, Ma=0.31 and Kn=0.08.

Ideally, with this design, 5 nm spherical particles should be focused to the lens axis if diffusion is absent. To verify the accuracy of the above design calculations, we carried out numerical simulations of gas flow and particle motion through this aerodynamic lens. Details of the simulation method are described below. A mass flowrate boundary condition was applied at the lens inlet, and an outlet pressure (159.2 Pa calculated from Equation (4)) was imposed at the outlet.

Figure 11A:
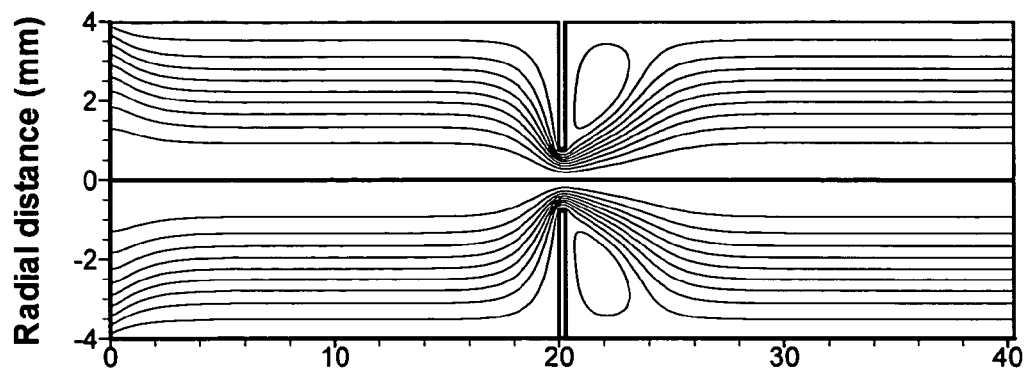
FIG. 11 shows (a) flow streamlines in an aerodynamic lens designed to focus 5 nm spherical unit density particles, and (b) static pressure and axial flow velocity along a lens axis.
Figure 11B:
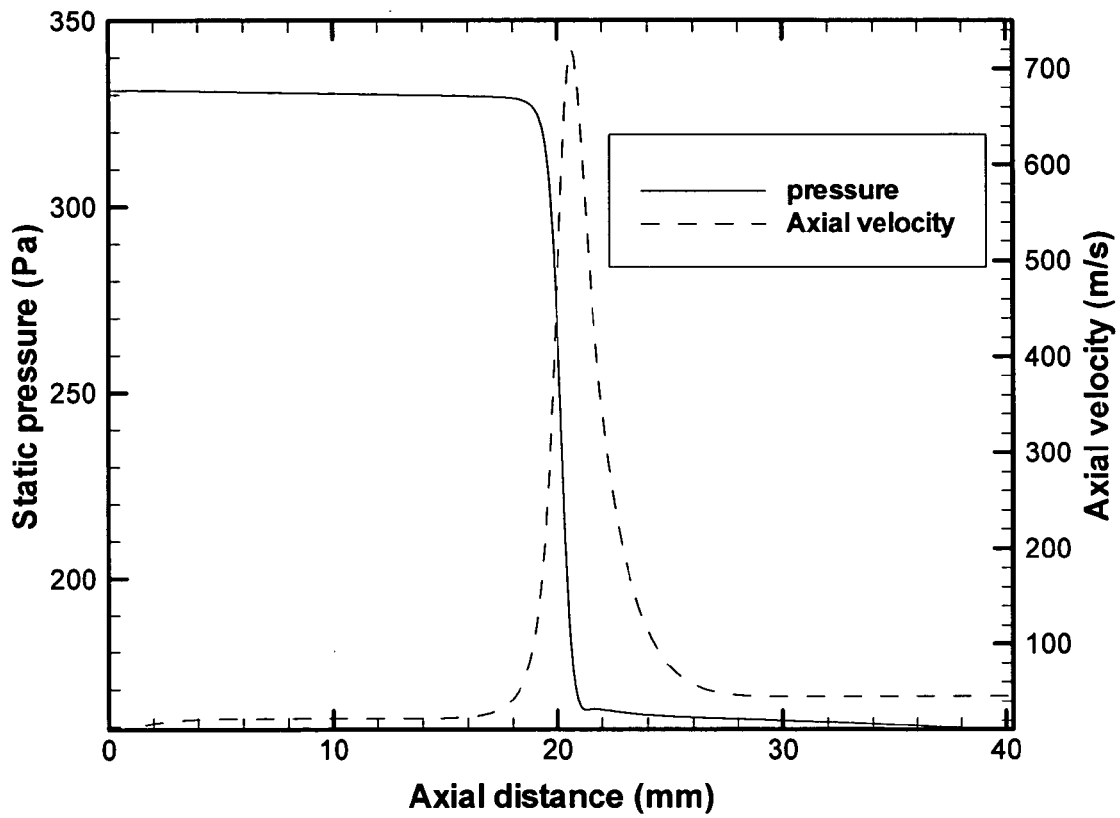
Figure 12A:
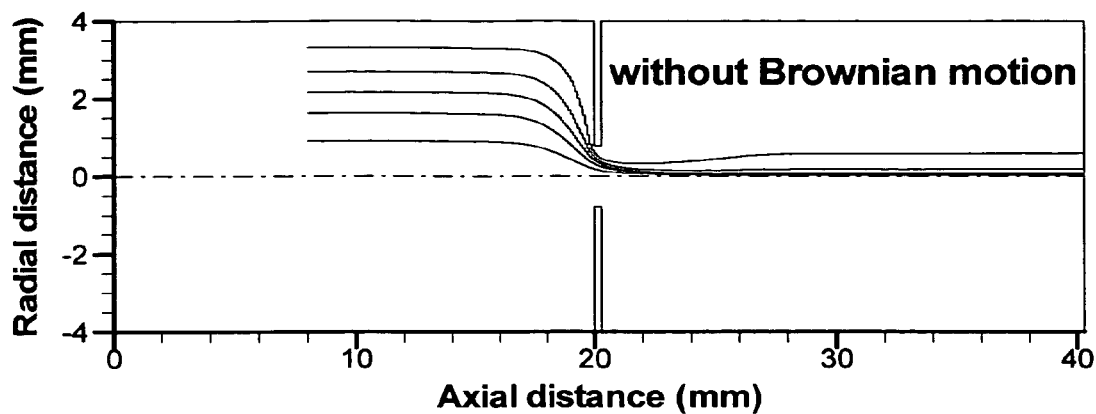
FIGS. 12a-b show shows trajectories of 5 nm spherical particles of unit density in the aerodynamic lens when Brownian motion is absent or present.
Figure 12B:
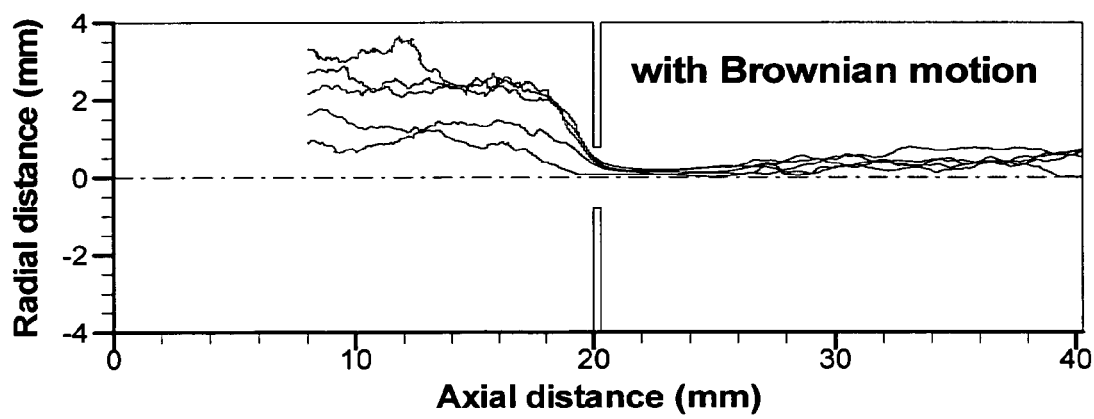
Figure 13A:
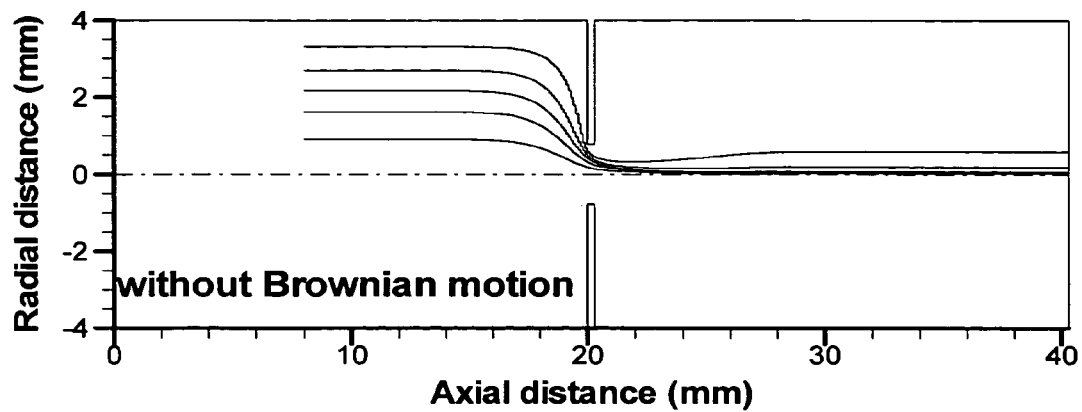
FIGS. 13a-b show trajectories of 2.1 nm spherical silicon particles in an aerodynamic lens designed for focusing 5 nm particle of unit density when Brownian motion is absent or present.
Figure 13B:
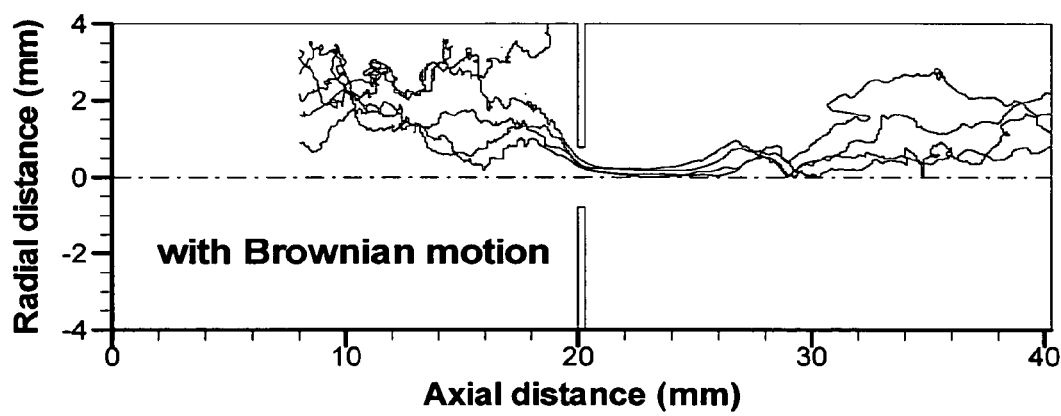
Figure 14A:
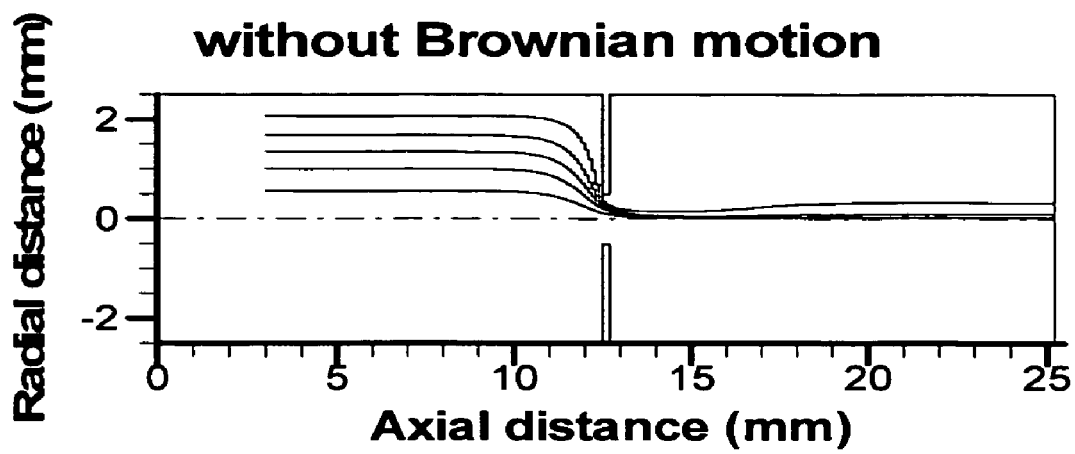
FIGS. 14a-b show trajectories of 5 nm spherical silicon particles in an aerodynamic lens designed for focusing 5 nm silicon particles when Brownian motion is absent or present.
Figure 14B:
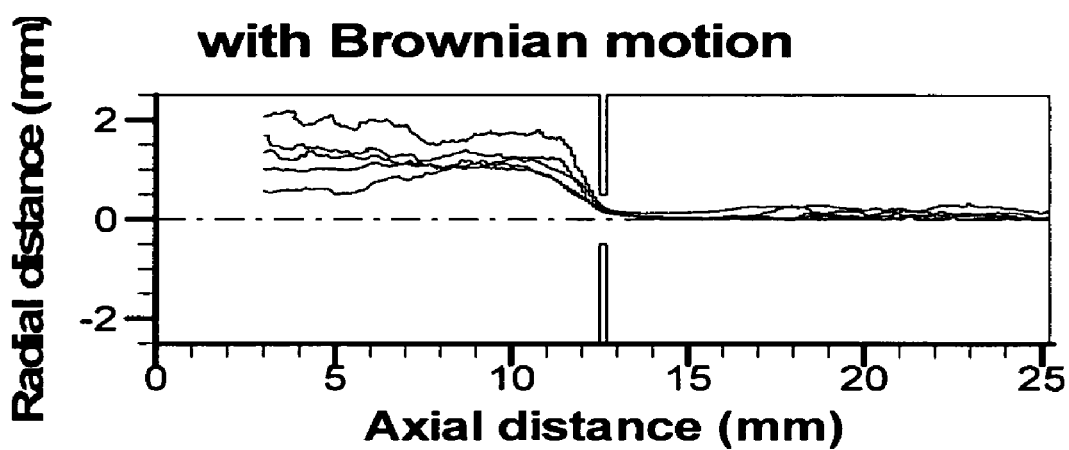

Flow streamlines are shown in FIG. 11a, and the static pressure and axial gas velocity along the lens axis are shown in FIG. 11b. Note that the flow becomes fully developed again about 8 mm downstream of the orifice. There is a significant pressure drop across the orifice. The simulated pressure at the lens inlet is about 332 Pa. This is about 8.4% higher than the value calculated from Equation (4) (304.2 Pa). It follows that the Stokes number of 5 nm particles is actually 0.55 rather than 0.6.

Trajectories of 5 nm particles with Brownian force absent or present are shown in FIG. 12. Note that when diffusion is absent, 5 nm particles initially located near axis can be focused very close the axis. Because of the underestimation of pressure drop in the design calculation, the optimally focused particle size shifts to 5.5 nm. Our simulation shows that the near-axis contraction factors are 0.03 for 5 nm and 0.001 for 5.5 nm (not shown in Figures) when diffusion is absent. Particles far from the axis are not focused as well, because velocities and therefore the Stokes numbers of these particles are smaller due to viscous effects (Liu et al. 1995a). When Brownian motion is present, although the particle beam is broadened to some extent, the focusing effect is still evident.

In short, aerodynamic lens systems can be designed to overcome the small inertia and high diffusivity of nanoparticles and focus them into collimated particle beams. We first developed a new model for flow through thin plate orifices, so that the pressure drop and mass flowrate through orifices can be estimated within±10%. Then we derived the minimum particle sizes that can be focused to the centerline with a single aerodynamic lens when diffusion is absent and when flow is continuum and sonic. We showed that lighter carrier gases are preferred to focus smaller sizes, and pointed out that multiple lenses working at sub-optimal Stokes numbers can be designed to focus particles smaller than the above-mentioned minimum sizes. The design of operating conditions for focusing nanoparticles was then discussed in detail. We found that there exists a maximum operating pressure that minimizes particle diffusion and pumping speed, just prior to the transition from subsonic to sonic flow. Finally, we illustrated the design process with an example of an aerodynamic lens to focus 5 nm particles. Numerical simulations verified the accuracy of the design calculations.

These design guidelines apply to particles of any density. The Stokes number that controls particle focusing in the absence of diffusion is approximately proportional to $\rho_p d_p$ (Equation (1)). Therefore, as particle density increases, the particle size that can be inertially focused for a given lens design decreases. On the other hand, when diffusion is present, Equation (13) shows that the diffusion coefficient is independent of $\rho_p$ but increases rapidly with decreasing $d_p$. Therefore, if 3 nm particles with density of 1 g/cm$^3$ can be focused in a lens system, it does not follow that a 1 nm particle with density of 3 g/cm$^3$ can be focused with the same system. Trajectories of 2.1 nm silicon particles in the lens designed for 5 nm particles with unit density are shown in FIG. 13. As silicon has a density of 2.33 g/cm$^3$, the Stokes numbers of 2.1 nm silicon particles are the same as those of 5 nm particles with unit density. We can see that particle trajectories are approximately the same in FIGS. 12 and 13 when Brownian motion is absent. However, due to the higher diffusion coefficient of smaller particles, particle penetration is lower and beam is broader in FIG. 13 when Brownian motion is present. We also note that for a given particle size, higher particle density permits lenses to operate at higher pressures, which results in less diffusion and better focusing. For example, the pressure upstream of the orifice can be as high as 907 Pa when an aerodynamic lens is designed to focus 5 nm silicon particles. FIG. 14 shows trajectories of 5 nm spherical silicon particles in such an aerodynamic lens. Note that the diffusion effects are less compared to those in FIG. 12.

Some examples described herein involve circular orifices or apertures through which the particles pass. Other shapes and types of openings can be used. This includes, but is not limited to, rectangular slits, which may allow much larger flow rates. For example, a rectangular slit may be implemented in a "particle concentrator" to produce a sheet of focused particles. In lenses that have apertures with a noncircular geometry, the size most relevant for purposes of obtaining good focusing may be its width, as opposed to another dimension.

There will now be described an example of how a numerical simulation tool can be used to evaluate the performance of an aerodynamic lens system. The lens system was designed to focus 3 nm spherical unit density particles following the guidelines described above. Both diffusional particle loss and beam broadening inside the lens system and in the downstream expansion are addressed. Four critical performance characteristics of this lens assembly are discussed: particle penetration, beam width, terminal axial velocity, and divergence angle. We also compare the effects of carrier gas, particle density and lens design on the focusing performance of aerodynamic lens systems.

The numerical model utilized the commercial CFD software FLUENT version 6.1.22. Under typical operating conditions of aerodynamic lens systems, particle concentrations are low enough so that particle-particle interactions are negligible and the presence of particles does not affect the carrier gas flow field. Therefore, the particle-free gas flow (axisymmetric, steady, compressible, laminar and viscous) was first calculated by solving the Navier-Stokes equations. Then particles were introduced into the system to obtain their trajectories and velocities.

In order to study particle motion downstream of the accelerating nozzle, we included a vacuum chamber in our simulation. The pressure inside the chamber was assumed to be 1 Pa (with pressure outlet boundary conditions imposed at the boundaries of the chamber). A mass flowrate ($2.98\times10^{-7}$ kg/s corresponding to 0.1 slm helium) boundary condition was applied at the inlet to the lens assembly.

Particle trajectories were obtained with the Lagrangian approach. To accommodate the effect of Brownian diffusion in Lagrangian calculations, one needs to add the random Brownian force to Newton's equations of motion along with the deterministic drag (friction) term. The Brownian force arises as a result of the collisions of molecules with the particles and acts for the time corresponding to the time of contact during a collision (~picoseconds) (Chandrasekhar 1943; Grassia 2001). On the other hand, the friction or drag forces act over a much longer time scale, which is of the order of the inertial relaxation time of the particle (~microseconds). Thus, we have a situation in which the forces act on a broad range of time scales and the equations of motion cannot be solved practically using standard techniques such as molecular dynamics (MD) simulations (Allen and Tildesley 1987). A "Brownian dynamics" method is usually employed to solve the Langevin equation effectively and economically. The essence of the Brownian dynamics simulation lies in the fact that it can handle forces with time scales separated by a few orders of magnitude, when one form of motion is much faster than another (Gupta and Peters 1985).

The Langevin equation is simply Newton's equation of motion for the particle including inertia, friction, steady forces (absent in this study) and a random force which drives the thermal motion of the particle:

$$\frac{d\vec{u}_p}{dt} = \vec{F}_{drag} + \vec{F}_{bi}, \qquad [32]$$

$$\frac{d\vec{x}}{dt} = \vec{u}_p, \qquad [33]$$

where $\vec{u}_p$ is the particle velocity vector, t is time, $\vec{F}_{drag}$ and $\vec{F}_{bi}$ are the drag and Brownian forces per unit mass, respectively, and $\vec{x}$ is the particle position vector. Note that the gas flow was laminar and particles were assumed spherical in this study. Therefore, turbulent dispersion and lift force were neglected. We should mention that neglecting lift forces is appropriate for spherical particles, but could lead to significant errors for nonspherical particles (Liu et al. 1995 a, b).

Because the Reynolds numbers of nanoparticles ($Re_p$) in aerodynamic lens systems are typically very small ($Re_p<1$), the drag force can be described by Stokes's law with the Cunningham slip correction (Hinds 1998):

$$F_{drag} = \frac{3\pi\mu d_p(u_f - u_p)}{m_p C_c}, \qquad [34]$$

where $\mu$ is the dynamic viscosity of the carrier gas, $d_p$ is particle diameter, $u_f$ is flow velocity, and $u_p$ is particle velocity, $m_p$ is particle mass, and $C_c$ is the slip correction based on local temperature and pressure.

By default, FLUENT assumes a constant Cunningham slip correction factor for a given particle size when calculating the drag force with the Stokes-Cunningham drag law. The default Brownian force in FLUENT utilizes this constant slip correction (FLUENT 2003). This assumption only works if the pressure and temperature along particle trajectories are constant. However, since there is significant pressure change in aerodynamic lens systems, the slip correction must be calculated using the correct pressure and temperature values along particle trajectories. We have used user-defined functions to calculate the drag force and Brownian force on particles.

The properties of the Brownian force per unit mass are described through the fluctuation-dissipation theorem (Grassia, 2001) by a Gaussian distribution with mean and mean-square values given by:

$$\langle F_{bi}(t) \rangle = 0, \qquad [35]$$

$$\langle F_{bi}(t) \cdot F_{bi}(t') \rangle = \frac{2kTf\delta(t'-t)}{m_p^2}, \qquad [36]$$

where the angular brackets denote averages, k is the Boltzmann constant, T is the local temperature, $f$ is the friction coefficient (Friedlander 2000), t and t' are times, and $\delta(t'-t)$ is the Dirac-delta function.

To construct a computer simulation of the Langevin description, the delta function of the white noise needs to be replaced by a numerical representation as $1/\Delta t$ (Grassia et al. 1995)

$$\delta(t'-t) = \begin{cases} 1/\Delta t & \text{if } t \text{ and } t' \text{ are in the time step } \Delta t \\ 0 & \text{otherwise} \end{cases} \qquad [37]$$

Thus, the Brownian force per unit mass in direction i at each time step can be rewritten as (Li and Ahmadi 1992; FLUENT 2003)

$$F_{bi} = G_i \sqrt{\frac{\pi S_0}{\Delta t}}, \qquad [38]$$

where $G_i$ represent zero-mean, unit-variance, independent Gaussian random numbers, and $$S_0 = \frac{216\nu kT}{\pi^2 \rho d_p^5 \left(\frac{\rho_p}{\rho}\right)^2 C_c}. \qquad [39]$$

Here $\nu$ is the kinematic viscosity, $\rho$ is the gas density, and $\rho_p$ is the particle mass density. Time steps in this simulation need to be small enough so that the drag force is approximately constant during $\Delta t$, and therefore the error in integrating the Langevin equation is small.

In this study the flow field was two-dimensional and axisymmetric. There was no flow in the azimuthal/tangential direction. However, in general, the random force has three components, corresponding to each of the three directions (x, y, z) in Cartesian coordinates. This implies that a three-dimensional study is required if one wants to have an accurate representation of the particle trajectories governed by deterministic and random forces, which would be computationally very expensive, especially for the flow field of interest i.e., the aerodynamic lens system. It was assumed that if there was no flow in the azimuthal direction, the trajectory calculation in the (x, r) plane would suffice to give a statistically sound result for the width of the particle beam as the particles traverse the aerodynamic lens system. Hence, the random force was generated with components in axial and radial directions only.

To validate the user-defined drag and Brownian forces, we ran a simulation of particle transport through a tube with low pressure (300 Pa) and laminar flow without axial diffusion. The penetrations were found to agree (±7%) with those predicted by the Gormley-Kennedy equation (Gormley and Kennedy 1949).

Figure 15:
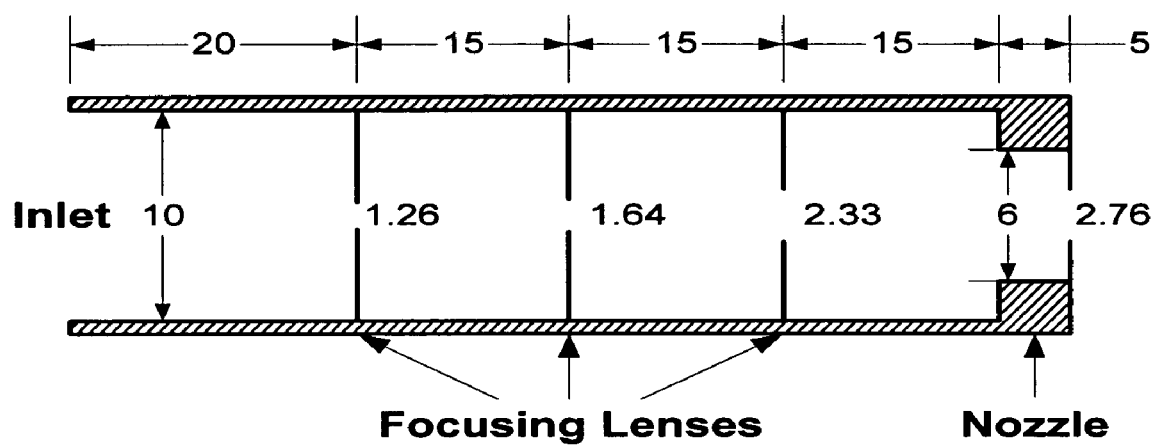
FIG. 15 shows a schematic of an aerodynamic lens assembly designed to focus 3 nm spherical unit density particles. The dimensions are in mm. The orifice plates are 0.3 mm thick.

We will now describe an example of designing the lens assembly to focus 3 nm spherical unit density particles using the guidelines described above. We have shown in Table 2 above-that with hydrogen, 3 nm particles could be focused to the lens axis with a single lens if diffusion is neglected. However, since hydrogen is flammable and potentially dangerous, we choose helium as the carrier gas. Although the minimal focusable size with a single lens in helium is 4.5 nm for spherical unit density particles, we can use multiple lenses operating at sub-optimal Stokes numbers to focus particles smaller than 4.5 nm. Using helium has the additional advantage of accelerating nanoparticles to higher axial velocities downstream of the nozzle compared to heavier gases, which reduces particle beam broadening in the vacuum chamber. The design process utilized the software for designing and evaluating aerodynamic lenses developed by the inventors. Using the design procedure described above, we chose an aerosol flowrate of 0.1 slm and the pressure before the accelerating nozzle to be 100 Pa. We found that three lenses were sufficient to achieve a contraction factor of 0.025 for 3 nm particles when diffusion was absent. A schematic of this lens system with key dimensions is shown in FIG. 15. It is interesting to note that unlike "conventional" aerodynamic lenses, the lens apertures in this design increase from upstream to downstream. This is because the lenses were designed to operate with large pressure drops. The pressures downstream were lower, and thus larger orifice sizes were required to maintain the Stokes number at a specific value while retaining subsonic flow. The operating pressure, particle Stokes number at each lens and the corresponding contraction factor for 3 to 30 nm particles are given in Table 3.

TABLE 3

Operating pressure, particle Stokes number (St) and corresponding contraction factor ($\eta$) of the lens system designed to focus 3 nm spherical unit density particles

| | Lens number | | | |
|---|---|---|---|---|
| | 1 | 2 | 3 | Nozzle |
| Upstream pressure (Pa) | 481 | 285 | 168 | 100 |
| St ($\eta$) of 3 nm particles | 0.28 | 0.36 | 0.36 | 0.61 |
| | (0.34) | (0.24) | (0.24) | (0.00) |
| St ($\eta$) of 6 nm particles | 0.56 | 0.72 | 0.72 | 1.23 |
| | (0.05) | (−0.08) | (−0.08) | (−0.40) |
| St ($\eta$) of 10 nm particles | 0.93 | 1.20 | 1.20 | 2.04 |
| | (−0.22) | (−0.39) | (−0.39) | (−0.77) |
| St ($\eta$) of 20 nm particles | 1.87 | 2.40 | 2.40 | 4.09 |
| | (−0.70) | (−0.89) | (−0.89) | (−1.25) |
| St ($\eta$) of 30 nm particles | 2.80 | 3.60 | 3.60 | 6.13 |
| | (−1.00) | (−1.17) | (−1.17) | (−1.42) |

Note that the total contraction factors of the three lenses are less than 1 except for 30 nm particles. However, later simulations showed that the pressure drops were slightly underestimated in this design calculation, and the operating pressures were 5%-10% higher than the values given in Table 3. This adjusted the Stokes number of 30 nm particles into a range where they could be focused. We should note that the concept of contraction factor is not valid for the nozzle in this case, because the pressure downstream of the nozzle is so low that particles travel rectilinearly. However, the nozzle contraction factors shown in Table 3 provide a qualitative indication of the particle divergence angle after the nozzle.

Figure 16:
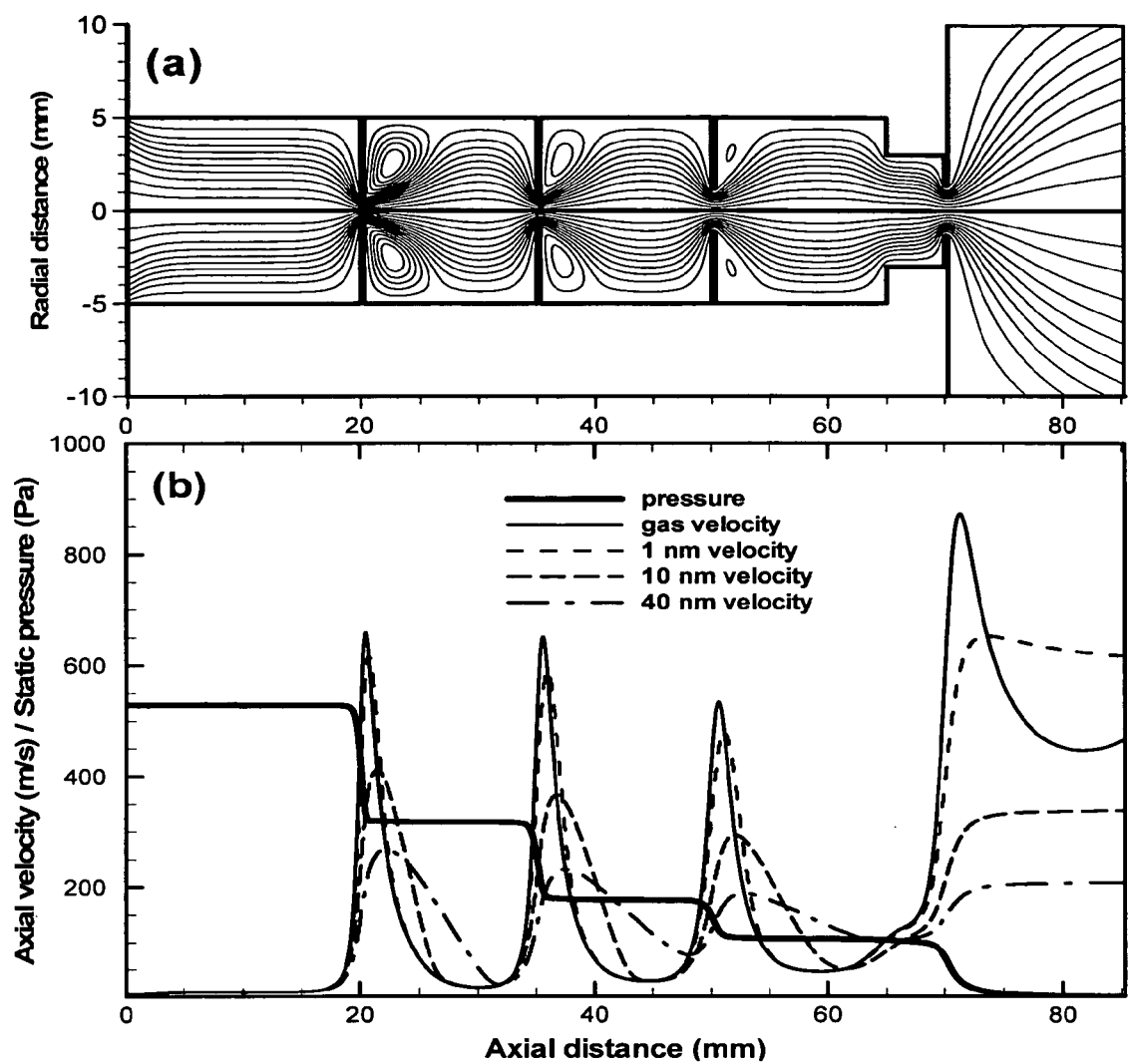
FIG. 16 shows (a) flow streamlines in a nanoparticle lens system; and (b) static pressure, axial flow and particle velocities along the axis of a nanoparticle lens system.
Figure 17A:
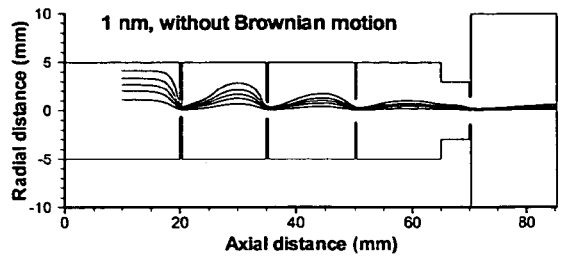
Figure 17B:
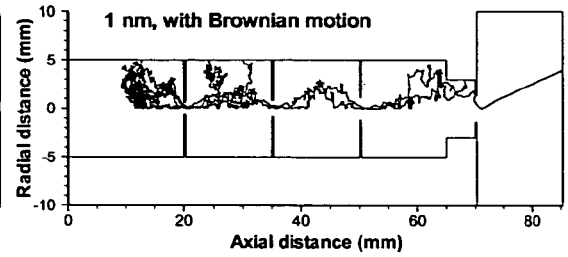
Figure 17C:
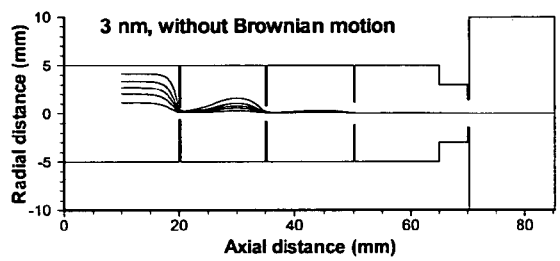
Figure 17D:
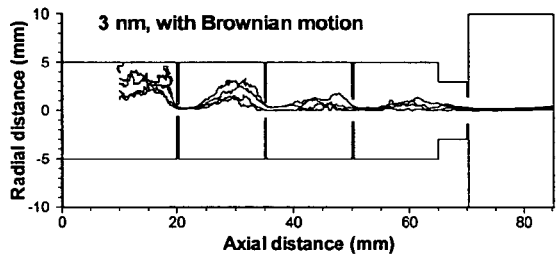
Figure 17E:
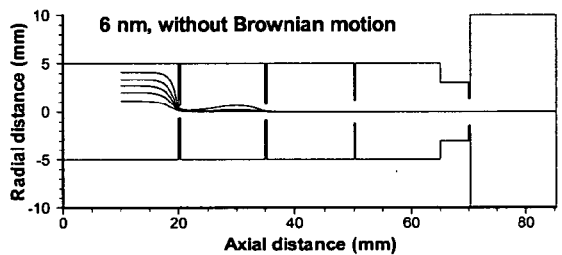
Figure 17F:
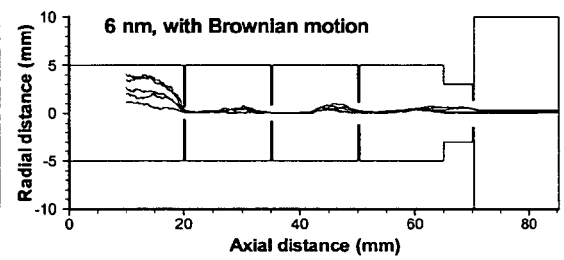

The numerical model was applied to evaluate the performance of the lens assembly designed in the preceding section. The flow streamlines are shown in FIG. 16a. The static pressure, axial flow velocity, and particle velocities for three sizes are shown in FIG. 16b. Note that because the lenses were designed to operate at high subsonic Mach numbers, there is significant pressure drop across the lenses. The flow velocity increases to about the speed of sound within about one nozzle diameter downstream of the nozzle exit, and the static pressure drops quickly to the chamber background pressure. It should be mentioned that the flow Knudsen number based on the chamber diameter is on the order of 1 at the pressure of 1 Pa. Therefore, these solutions to the Navier-Stokes equations may not accurately represent the flow field in this low pressure regime. Fortunately, the flow field at this low pressure does not significantly affect particle motion, which is of most interest to us. Because the drag force and Brownian forces are negligibly small at this low pressure, particles essentially travel rectilinearly with their terminal velocities. FIG. 16b shows that particle axial velocities approximately remain constant about 2 nozzle diameters downstream of the nozzle exit.

Simulated particle trajectories with the Brownian force absent or present are shown for six particle sizes in FIGS. 17a-l. For illustrative purposes, only five particles were injected at a cross section 10 mm downstream of the inlet. Since the geometry is axisymmetric, only particles above the axis are shown. A mirror reflection boundary condition of particles was imposed on the axis. Note that a fairly tight particle beam of 1 nm particles can be generated with this lens system when Brownian diffusion is absent. However, most particles deposit onto walls due to diffusion before they reach the exit if diffusion is present. The single 1 nm particle that survived in this simulation travels in the vacuum chamber with a large divergence angle (defined as the angle between the final particle trajectory and the axis of the lens system). Diffusional broadening is still significant for 3 nm particles, but particles are consistently moved closer to the axis, and losses to the wall are substantially reduced. For particles larger than 30 nm, no significant difference is observable in particle trajectories when diffusion is absent or present. One can clearly see that larger particles (30 nm) cross the axis (shown as reflected from the axis) due to their high Stokes numbers. Many of the largest particles (50 nm) impact on the orifice wall and are lost.

Figure 18:
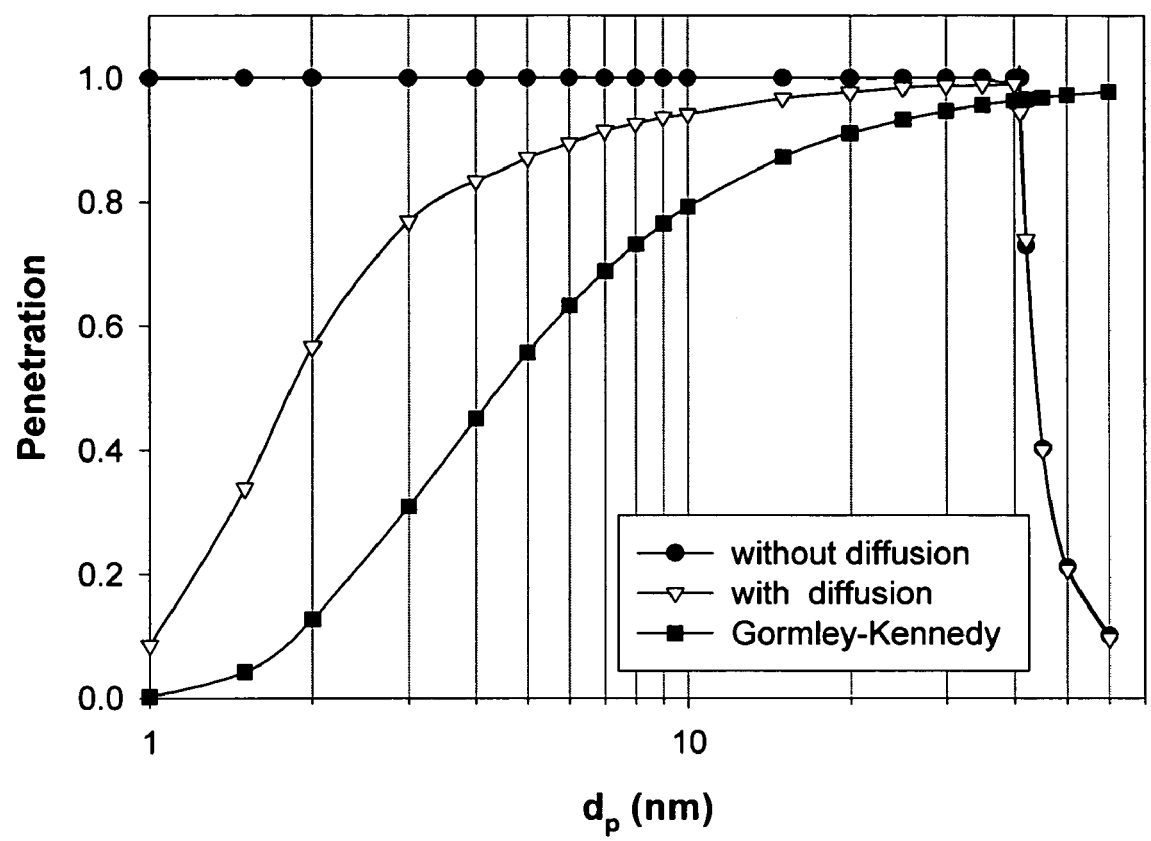
FIG. 18 shows a comparison of particle penetration through a nanoparticle lens system when Brownian motion is included or absent and estimation using the Gormley-Kennedy equation (Gormley and Kennedy 1949).
Figure 19A:
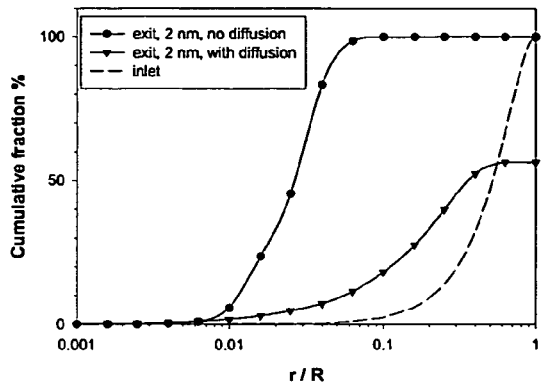
FIG. 19 shows cumulative fraction of particles within the radial distance shown in the abscissa when diffusion is absent and when diffusion is present (R=5 mm for the inlet curve, and R=1.38 mm for the exit curves). For each particle size, results are shown for the inlet to the lens assembly and at the exit from the nozzle.
Figure 19B:
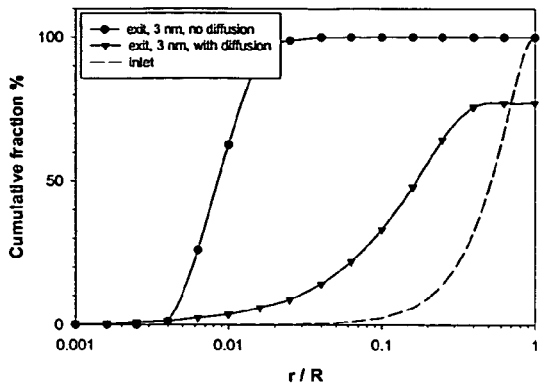
Figure 19C:
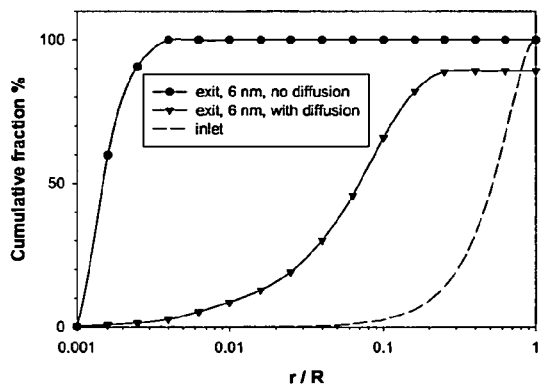
Figure 19D:
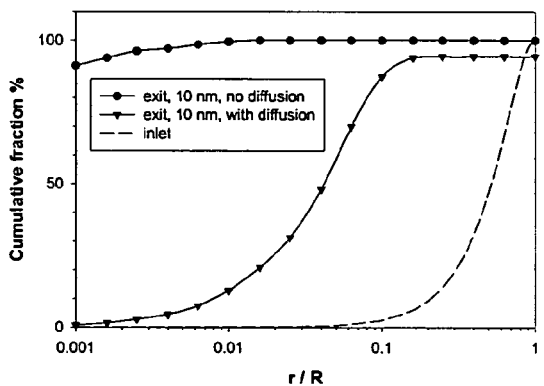
Figure 19E:
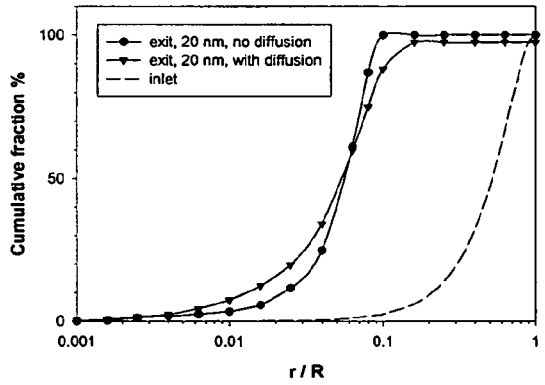
Figure 19F:
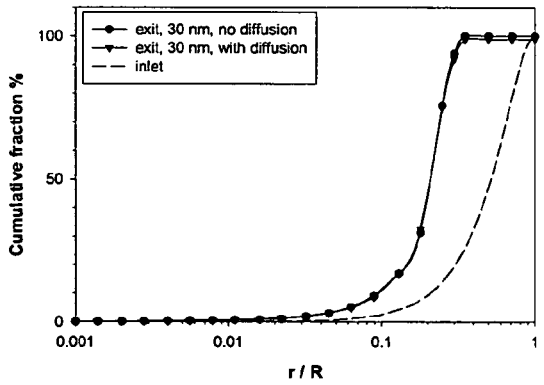
Figure 20:
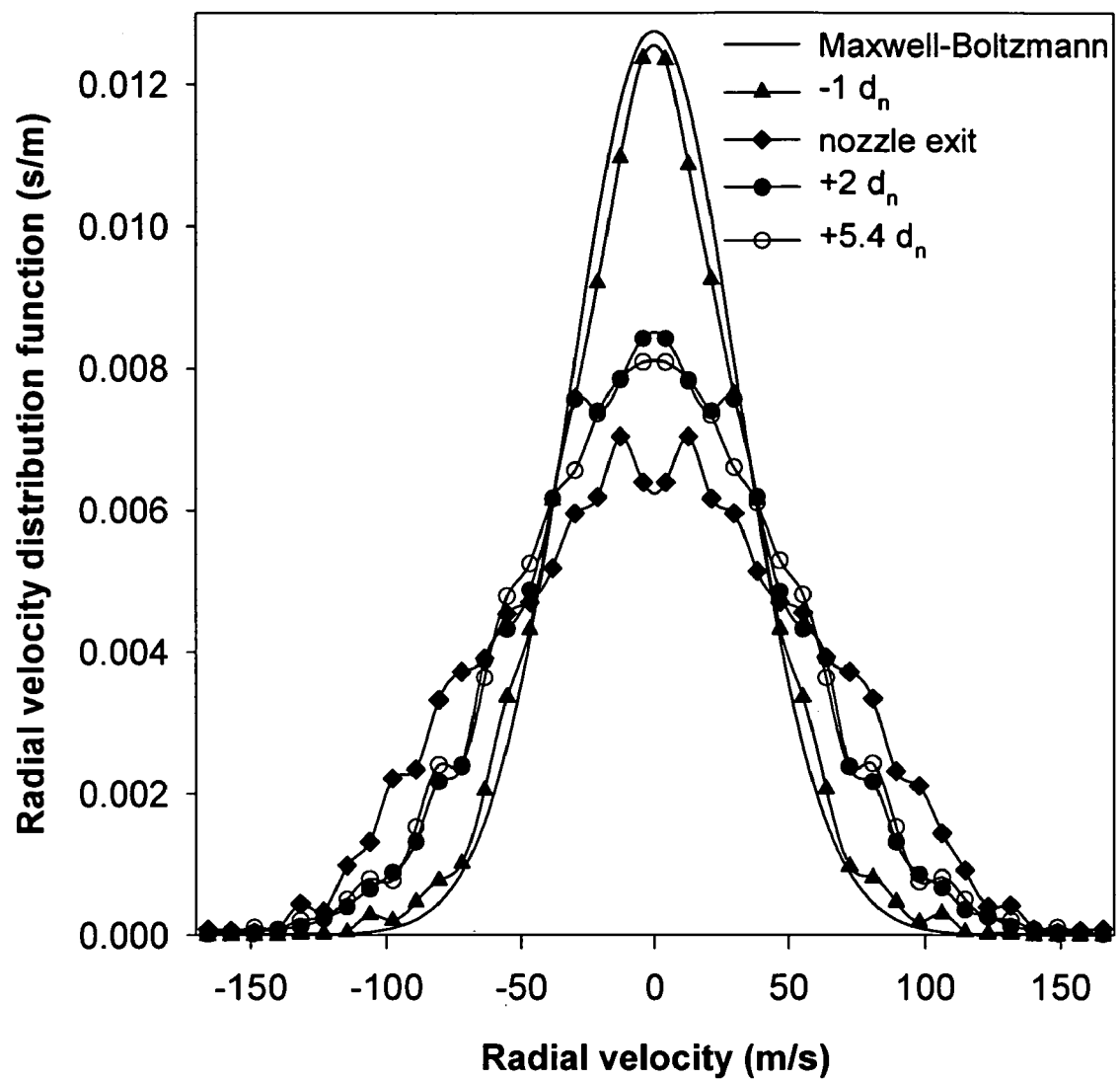
FIG. 20 shows evolution of 2 nm particle radial velocity distribution functions at four axial locations: one nozzle diameter upstream of the nozzle exit, at the nozzle exit, and 2 and 5.4 nozzle diameters downstream of the nozzle exit. Also shown is the Maxwell-Boltzmann velocity distribution function of 2 nm unit density particles at 296.15 K.
Figure 21:
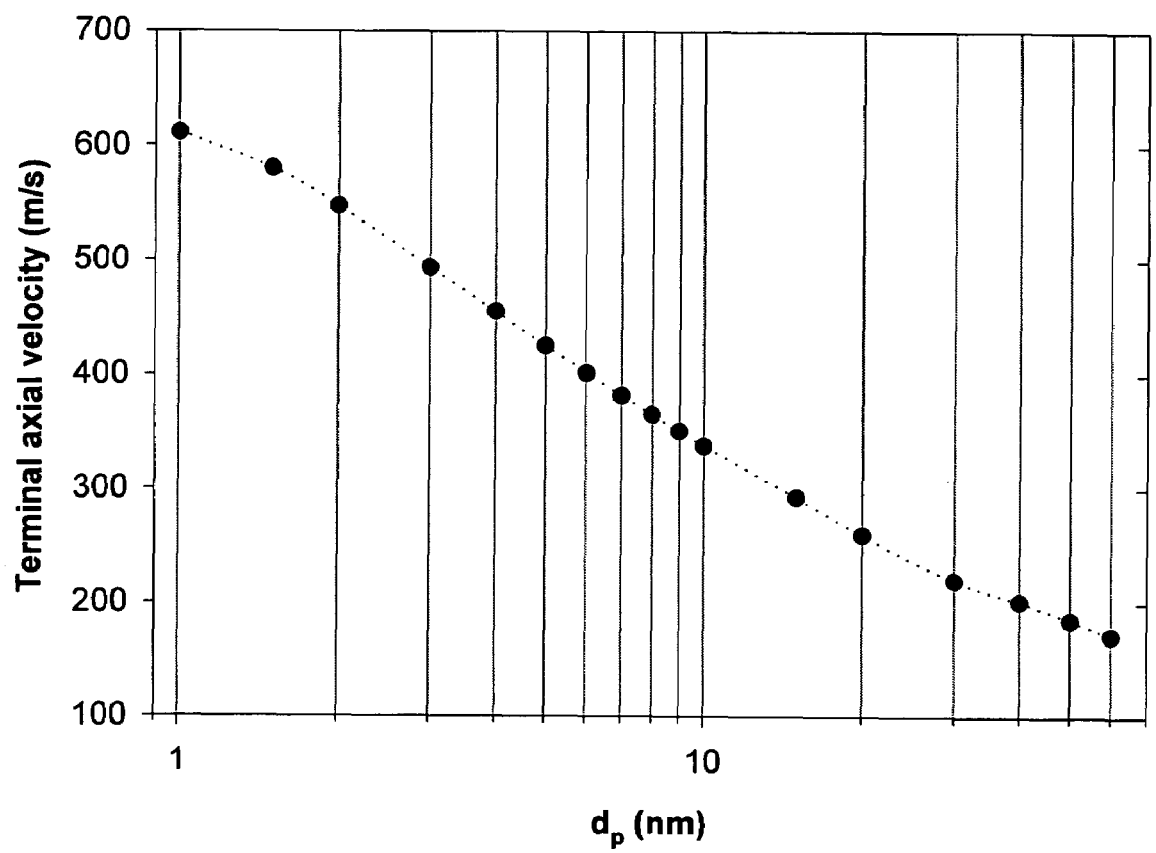
FIG. 21 shows averaged particle axial terminal velocity.
Figure 22A:
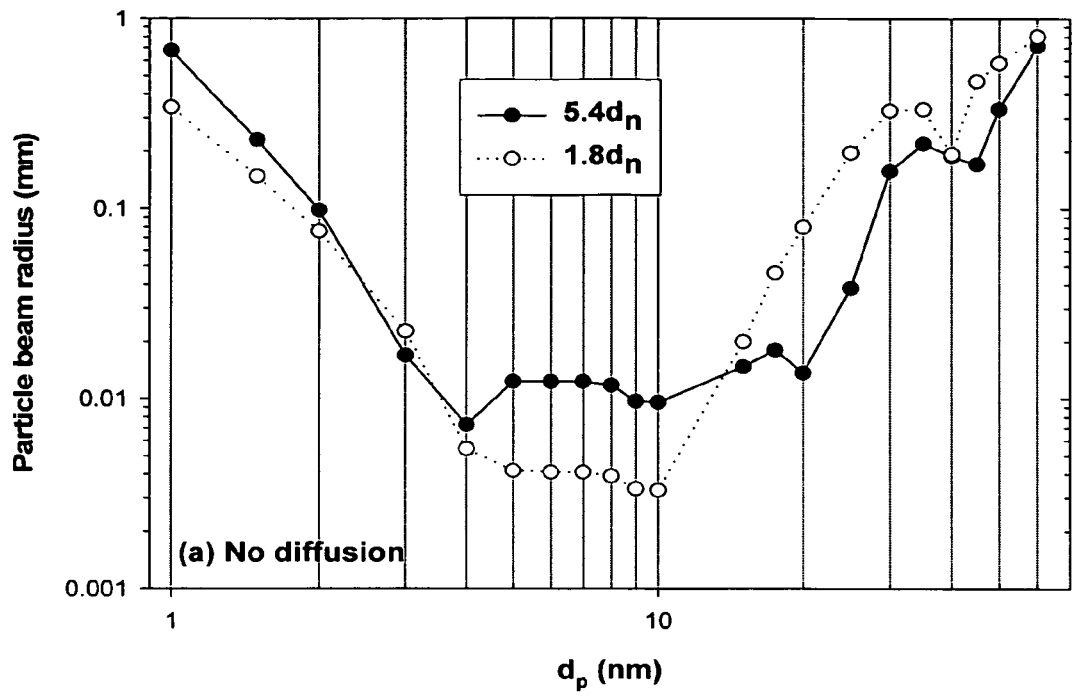
FIG. 22 shows particle beam width in the vacuum chamber 1.8 and 5.4 nozzle diameters downstream of the nozzle exit: (a) without diffusion; and (b) with diffusion.
Figure 22B:
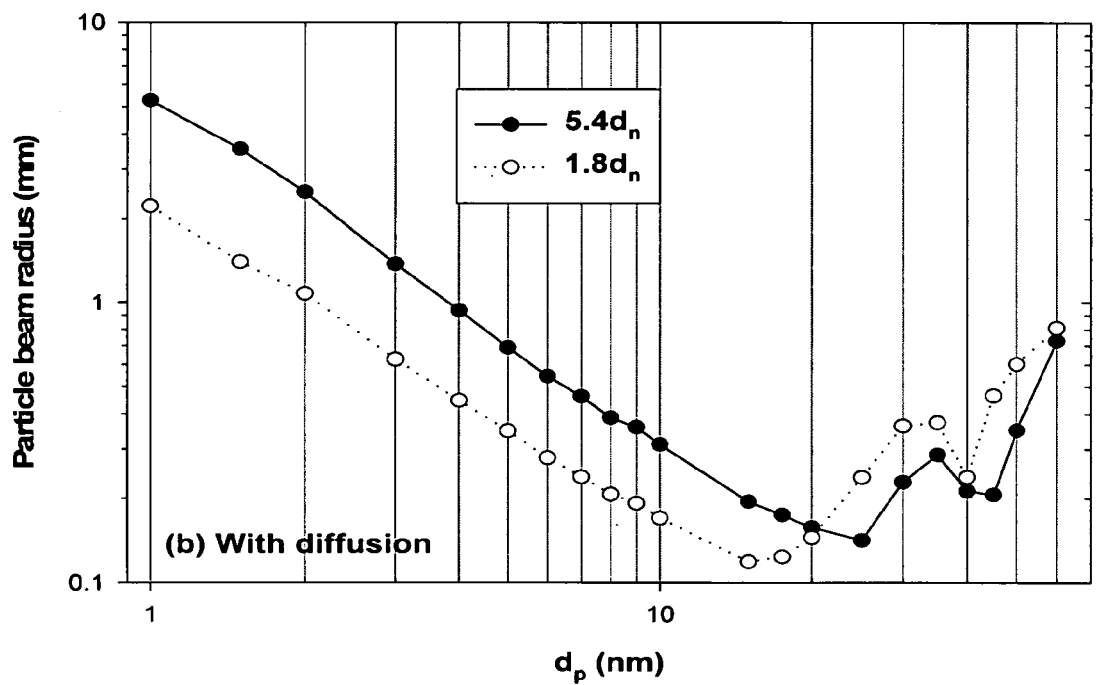
Figure 23:
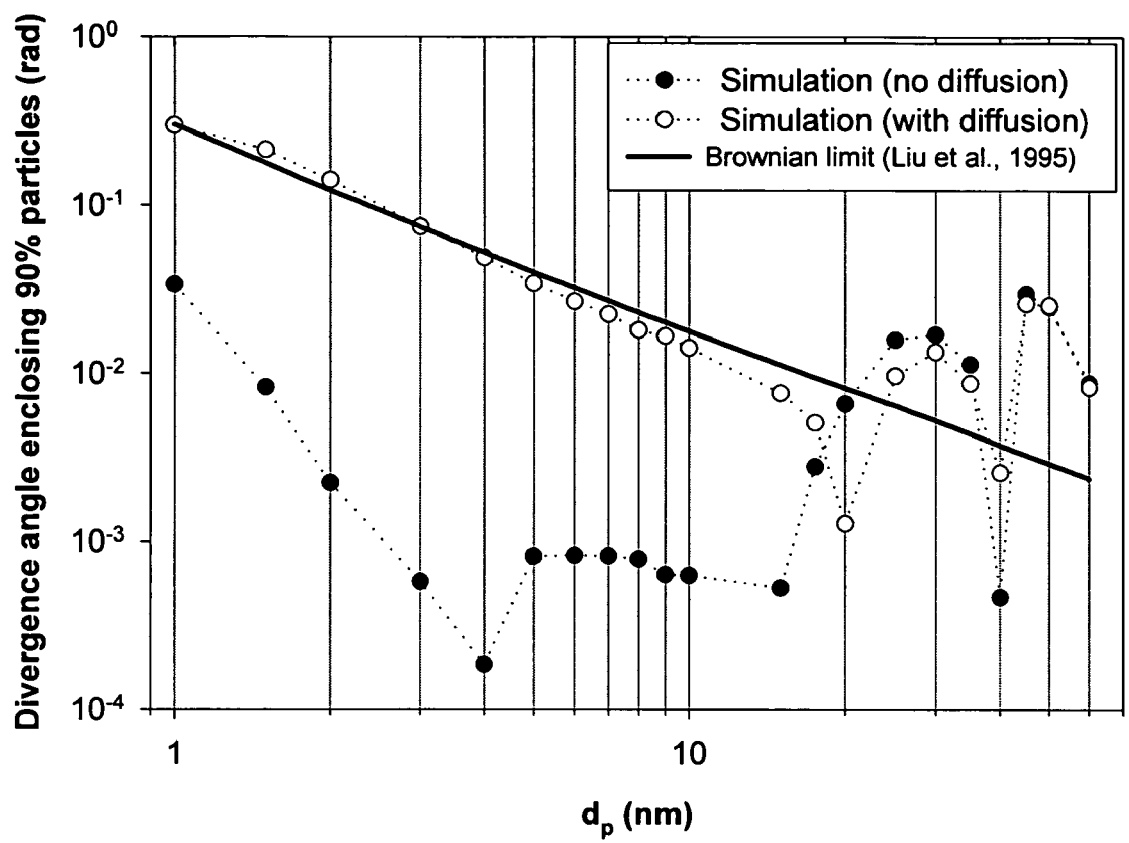
FIG. 23 shows particle beam divergence angles estimated from the Brownian limit proposed by Liu et al. (1995a) and from current simulations with diffusion present or absent.
Figure 25:
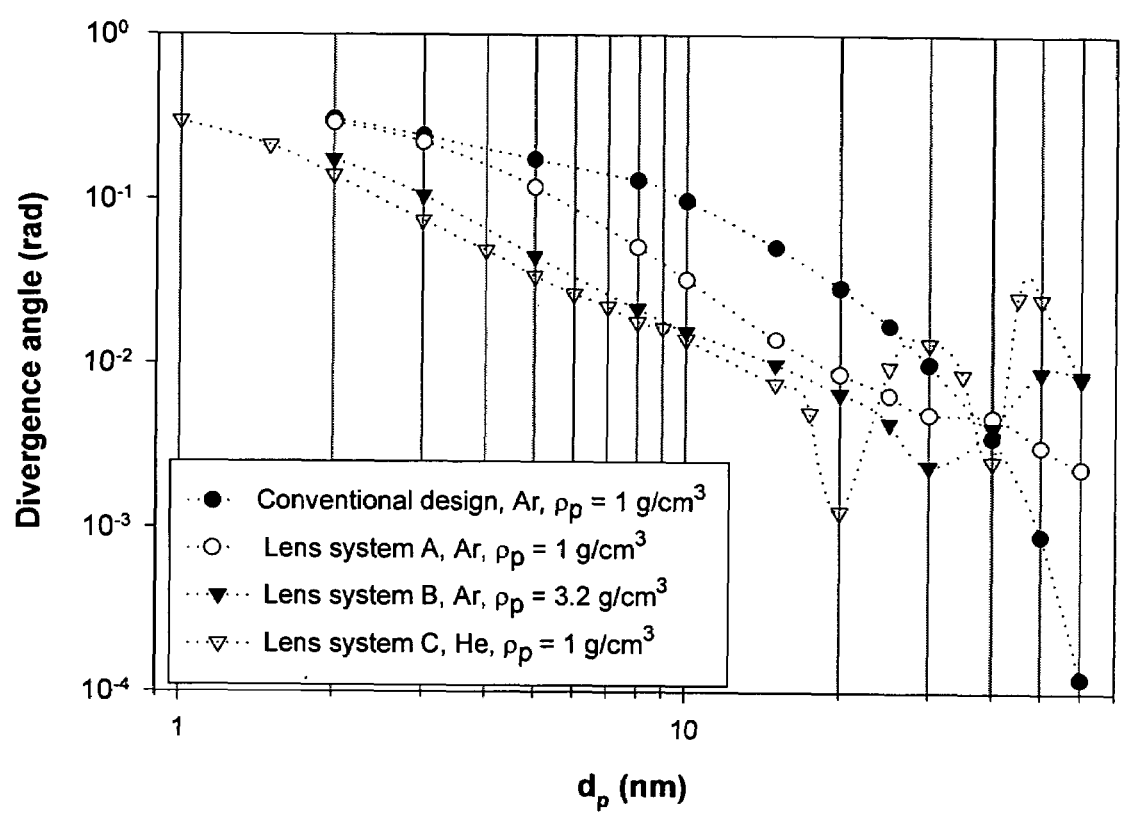
FIG. 25 shows a comparison of the divergence angle of the particle beam generated by a "conventional" aerodynamic lens system and three nanoparticle lens systems for particles of different density using different carrier gases.

FIG. 18 shows simulated particle penetration through the focusing apparatus when Brownian motion is absent or present. To obtain statistically significant results, a total of 5000 particles were injected in a plane 10 mm downstream of the inlet, with particles distributed radially to provide constant particle flux. The penetration is defined as the ratio of the number of particles exiting the accelerating nozzle to the number entering the inlet. Note that the diffusional losses become significant for particles smaller than 10 nm. However, the penetration of 2 nm particles is predicted to be 56.3%, which is still much higher than predicted by the Gormley-Kennedy equation (12.8%) assuming that the apparatus can be modeled as a c nozzle exit. The radial velocity distribution function f(v)dv is defined as the fraction of particles in the radial velocity range [v, v+dv]:

$$f(v) = \frac{dN}{Ndv}, \quad [40]$$

where dN is the number of particles in the velocity range [v, v+dv] and N is the total number of particles. The Maxwell-Boltzmann velocity distribution of 2 nm particles of unit density at 296.15 K is also shown in FIG. 20 for comparison. Note that at one nozzle diameter upstream of the nozzle exit ($-1d_n$), the simulated particle velocity distribution is very close to the Maxwell-Boltzmann distribution, indicating particles are in equilibrium with the fluid flow in the radial direction. Particles are accelerated towards the axis near the exit aperture, creating a wider velocity distribution at the nozzle exit. This inward acceleration is counteracted by the rapid expansion downstream of the exit, thus the velocity distribution narrows again. Note that the velocity distribution at 2 nozzle diameters ($2d_n$) downstream is approximately identical to that at 5.4 nozzle diameters downstream ($5.4d_n$). This is because the velocity distribution is "frozen" in the low pressure region due to low frequency of collisions with gas molecules. From the particle axial velocity evolutions shown in FIG. 16b, and the radial velocity evolution in FIG. 20, we can see that it is reasonable to assume that most particles reach their terminal velocities at about 2 nozzle diameters downstream of the nozzle exit. Simulated particle axial terminal velocities averaged over all particles exiting the nozzle are shown in FIG. 21. Note that particle velocity is a strong monotonic function of particle size. This is a desirable feature in many time-of-flight instruments that infer particle sizes from their velocities. It has been shown that if a capillary is used instead of a thin plate orifice as the accelerating nozzle, particle velocities are higher and less dependent on size (Mallina et al. 1997). This would be advantageous in some other applications such as micro-device fabrication (Di Fonzo et al. 2000), since the higher velocities reduce flight time and therefore reduce the beam broadening downstream of the nozzle. Furthermore, higher velocities can decrease the impaction cut size.

In this design, we have tried to focus particles as much as possible before they reach the accelerating nozzle so that the particle beam will not expand severely downstream of the nozzle. Particles may be further focused or defocused by the nozzle as indicated by the contraction factors shown in Table 3. After particles reach terminal velocities, their trajectories can be characterized by starting radial locations and divergence angles. Ideally, the divergence angle of a particle beam will be approximately constant only after all particles are moving away from the axis. However, this condition would require a very large computational domain. To get a simple estimate of the tangent of the divergence angles that contains 90%. of total particles (which defines the diameter of the particle beam) we first calculated the radii of the particle beam at two planes with axial distances of 75.3 mm and 85.3 mm from the inlet, which correspond to 1.8 and 5.4 nozzle diameters downstream of the nozzle exit, respectively. Then we divided the difference of these two beam radii by the distance between the two planes (10 mm). We should note that divergence angles obtained in this way are different from those reported by Liu et al. (1995a), who assumed that all particles are on the axis at the exit of the nozzle. In our calculation, the finite width of the particle beam at the plane of $1.8d_n$ downstream of the exit of the nozzle was accounted for. Furthermore, a fraction of the particles cross the axis downstream of the nozzle. These particles end at radial positions closer to the axis than if they had initially moved away from the axis at the same radial speed. Therefore, our divergence angles are somewhat smaller than those reported by Liu et al. (1995a).

FIG. 22 shows simulated radii of particle beams for 1-60 nm particles at planes $1.8d_n$ and $5.4d_n$ downstream of the nozzle exit (a) with diffusion neglected and (b) with diffusion considered. Note that the curves in FIG. 22 a have a "U" shape. This can be readily explained by the relation between contraction factor and Stokes number (FIG. 6). The difference in beam width at the two planes can be explained by whether or not particles cross the axis and where they cross the axis, depending on the competition between the particle inertial focusing at the nozzle and the outward acceleration downstream of the nozzle. A detailed explanation was given by Zhang et al. (2004) with the aid of representative particle trajectories. Although our situation is more complicated because we are tracking the whole particle beam instead of a single particle, we will not repeat the explanation for the sake of simplicity. The important point to note is that, by comparing FIGS. 22*a* and 22*b*, diffusion is the dominant factor that determines the beam width for particles smaller than 30 nm. The particle beam widths for these sizes increase about an order of magnitude when diffusion is considered.

FIG. 23 compares the particle beam divergence angles obtained from FIG. 22 with those predicted by the Brownian limit (Equation (25)). Although the gas temperature momentarily drops down to 225 K in the rapid expansion region, particle temperatures remain approximately constant (296.15 K) because the low gas pressure and short residence time in the cold region prevent significant cooling. A frozen temperature $T_{pF}$=296.15 K was assumed in the Brownian limit calculation. Note that when diffusion is absent, the particle beam divergence angles for small particles are much smaller than the Brownian limit. The larger divergence angles for the smallest and largest sizes are due to the poor collimation of these sizes at the entrance to the nozzle (too small or too large Stokes numbers). When diffusion is present, the divergence angles increase drastically as particles become smaller than 20 nm. As was shown in FIG. 20, the terminal particle radial velocity distribution is wider than the Maxwell-Boltzmann distribution. This indicates that the simulated particle beam divergence angles when Brownian motion is present should be wider than the Brownian limit. However, FIG. 23 shows that the divergence angles of particles in the diameter range of 4-20 nm are smaller than the Brownian limit although they are very close. This is because the particles crossing the axis enhance particle concentrations closer to the axis according to our definition of divergence angle, as discussed earlier.

Since helium is not necessarily the carrier gas in experiments, and particles are not always of unit density, we finally compare the focusing performance of various aerodynamic lens systems designed for focusing sub-30 nm particles of different density using different carrier gases. Nanoparticle lens system A uses argon as the carrier gas and is designed for unit density particles, while lens system B uses argon as the carrier gas and is designed for a particle density of 3.2 g/cm$^3$. Lens system C is the one that is designed and described in detail here. It uses helium as the carrier gas for focusing unit density spherical particles. The dimensions and operating conditions of these three nanoparticle lens systems are listed in Table 4. Also listed is a "conventional" aerodynamic lens assembly (not optimized for nanoparticles) studied by Liu et al. (1995b). FIG. 24 compares simulated particle penetration through these four lens systems, and FIG. 25 shows simulated divergence angles of particle beams generated by these lens systems.

TABLE 4

Dimensions and operating conditions of a "conventional" aerodynamic lens system (Liu et al. 1995b) and three nanoparticle lens systems for focusing particles of different density using different carrier gases.

| | Lenses | | | |
|---|---|---|---|---|
| | Conventional lenses | Nanoparticle lenses A | Nanoparticle lenses B | Nanoparticle lenses C |
| Carrier gas | Ar | Ar | Ar | He |
| (molecular weight) | (39.948) | (39.948) | (39.948) | (4.003) |
| Flow rate (slm) | 0.1 | 0.1 | 0.1 | 0.1 |
| Particle density (g/cm$^3$) | 1 | 1 | 3.2 | 1 |
| Inlet pressure (Pa) | 296 | 324 | 254 | 528 |
| Lens diameters (mm) | 5.00 | 2.47 | 2.73 | 1.26 |
| (in the flow direction) | 4.50 | 3.07 | 3.64 | 1.64 |
| | 4.00 | 3.94 | 4.89 | 2.33 |
| | 3.75 | 4.99 | | |
| | 3.50 | | | |
| Nozzle diameter (mm) | 3 | 5.65 | 5.65 | 2.76 |

The first point to note is that although the "conventional" lens assembly has high penetration and low divergence angle for particles larger than 50 nm, it has the lowest penetration and the largest divergence angle for sub-20 nm particles among the four lens systems in comparison. This observation indicates that the lens systems designed according to our guidelines for focusing nanoparticles as described above have superior performance to the "conventional" lens assembly for focusing nanoparticles. A close look at the divergence angles of the "conventional" lens system and nanoparticle lens system A shows that the divergence angle is reduced by more than 60% with nanoparticle lens system A for particles in the diameter range of 8-30 nm, while the reduction is less than 9% for particles smaller than 3 nm. Note also that the divergence angles of particles less than 5 nm are still more than 0.11 rad (6.3°) even with the nanoparticle lens system A. Meanwhile, both lens assemblies have penetration lower than 50% for particles smaller than 3 nm. The main reason of the non-ideal focusing of sub-5 nm particles is the low particle inertia in the aerodynamic lenses with argon as the carrier gas. Since very little focusing is achieved, diffusion causes significant particle deposition. However, particle inertia increases with particle density. Therefore, better focusing can be attained for particles with higher density using the same carrier gas. Note that the nanoparticle lens system B, which is designed to focus particles of density 3.2 g/cm$^3$, has much higher penetration and lower divergence angle compared to the other two lenses with the same carrier gas (argon). As was pointed out above, a lighter carrier gas is preferred for focusing nanoparticles. Clearly the nanoparticle lens system C with helium as the carrier gas has far better focusing performance for particles in the size range of 1-20 nm than the other two lens systems designed to focus particles of the same density. Further improvements in focusing can be obtained for particles with density greater than 1 g/cm$^3$ using helium as the carrier gas.

Figure 24:
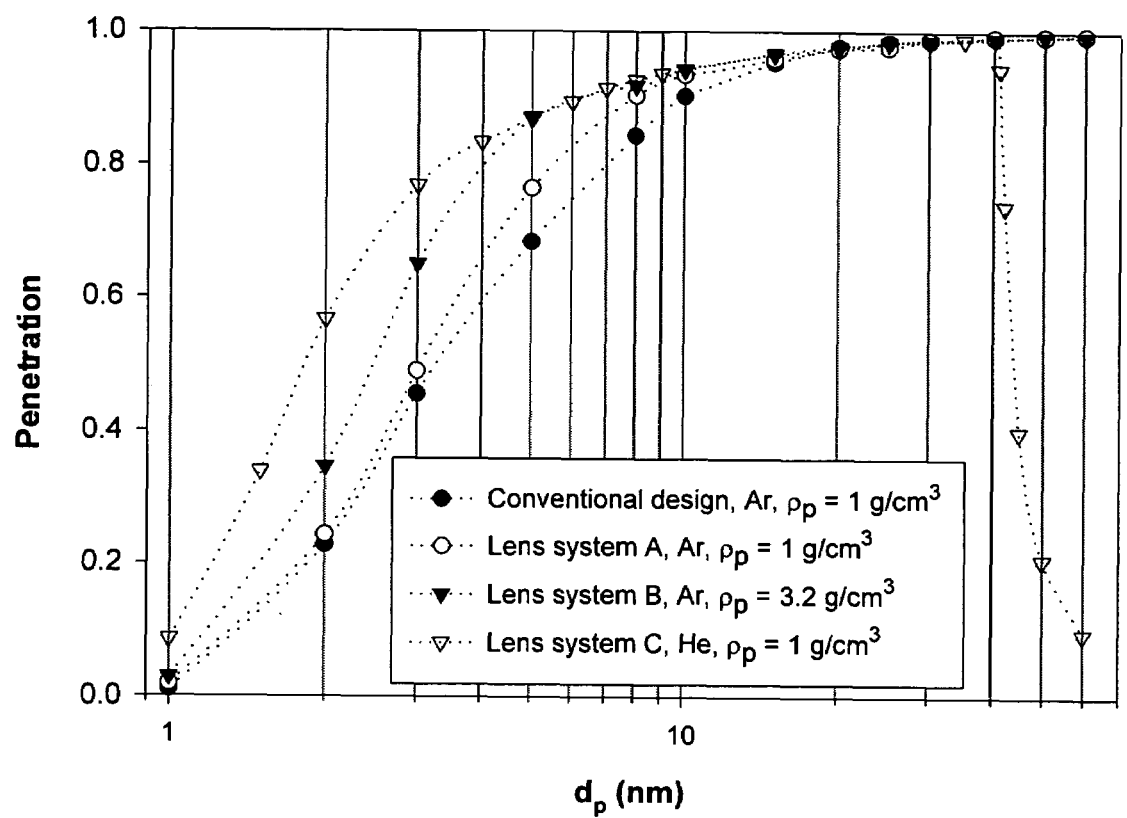
FIG. 24 shows comparison of particle penetration through a "conventional" aerodynamic lens system and three nanoparticle lens systems for particles of different density using different carrier gases.

As mentioned throughout this description, the ability to focus particles of very small dimensions can be important or essential in many areas. The necessary or desirable quality of focusing may depend on the particular implementation. The focusing may be measured by beam width, divergence angle and transport efficiency. In a specific situation, there may be established maximum or target values for the beam width and divergence angle, and a minimum or target transport efficiency. FIGS. 24 and 25 allow comparisons of focusing quality. The nanoparticle lens systems in FIG. 25 were optimized to focus 3-10 nm particles and their divergence angles are smaller than the "conventional" lens. In other implementations, such as those that are optimized for 30 nm particles, a greater reduction in divergence angle may be obtained.

Above has been described an exemplary numerical tool to characterize aerodynamic lens systems. This tool used the commercial CFD software FLUENT. The gas flow field was first obtained by solving the viscous laminar compressible Navier-Stokes equations. Particles were tracked with the Lagrangian approach assuming that the presence of particles did not affect the flow field and that there was no particle-particle interaction. User defined functions were used to calculate the drag force and Brownian force. This numerical tool was applied to evaluate an aerodynamic lens system designed to focus 3 nm spherical unit density particles.

The design of this lens system followed the guidelines described above. It used three lenses in series to focus 3 nm particles with sub-optimal Stokes numbers. The detrimental diffusion effects inside the lens system were minimized by maximizing the operating pressure, with each lens operating in subsonic flow but at higher Mach numbers. By using helium, higher axial velocities were achieved to reduce the beam broadening downstream of the nozzle.

Using numerical simulations we showed that there is a 5%-10% underestimation of operating pressure in the design calculation, which results in a slight shift to larger particles for focusing. Particle trajectories, penetration, velocity, beam width and divergence angles were studied. It was found that although most 1 nm particles are lost to walls by diffusion, penetrations of 2 to 40 nm particles are from 56% to 99%, with diffusional losses dominant for particles smaller than 10 nm and inertial impaction losses dominant for particles larger than 40 nm. We also compared particle penetration through the lens system with laminar flow penetration through a cylindrical tube of the same length, flowrate and pressure. This comparison showed that the aerodynamic lens system drastically reduces diffusional losses by moving particles away from walls. An investigation of particle radial distribution at the exit of the accelerating nozzle showed that all particles from 2 nm to 30 nm are focused to some extent even when diffusion is included in the simulation. Particles achieve their terminal velocity distribution about 2 nozzle diameters downstream of the nozzle exit, and their rectilinear trajectories can be characterized by divergence angles. We found that for sub-20 nm particles, while the particle divergence angles that enclose 90% of total particle flux with this lens system are much smaller than the Brownian limit when diffusion is absent, the simulated and predicted beam widths are very close when diffusion is present.

We also compared the particle penetration and beam divergence angle of a "conventional" aerodynamic lens assembly (not optimised for nanoparticles) with lens systems designed to focus nanoparticles. The effects of particle mass density and carrier gas were addressed. We showed that lens systems designed following the guidelines described above perform better than the "conventional" lens system for nanoparticle focusing. We demonstrated that nanoparticles with greater density are easier to focus, and better focusing can be achieved with lighter carrier gases.

In conclusion, our numerical model successfully simulated particle motion in aerodynamic lenses. A case study of using this tool to evaluate an aerodynamic lens assembly designed to focus 3 nm spherical unit density particles verified that the design guidelines provide an excellent approximation to the more accurate results obtained by numerical simulations. The simulations also demonstrated that aerodynamic lens systems can be properly designed to focus sub-10 nm particles.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus for shaping an aerosol beam having particles suspended in a gas, the apparatus comprising:
    an aerodynamic lens having an aperture therethrough, wherein a size of the aperture and an operating pressure of the aerodynamic lens are selected so that aerodynamic lens aerodynamically focuses at least some particles where a product of particle density and particle diameter is below about 20 nm·g/cm$^3$.

2. The apparatus of claim 1, wherein the aerodynamic lens operates at a suboptimal or optimal Stokes number.

3. The apparatus of claim 1, wherein the operating pressure at which the aerodynamic lens aerodynamically focuses the particles is selected such that it exists above a Mach limit pressure and above a Knudsen limit pressure.

4. The apparatus of claim 1, wherein the apparatus comprises at least one selected from the group consisting of: an apparatus for performing chemical analysis, a mass spectrometry apparatus, a particle deposition apparatus, a cluster beam apparatus, and combinations thereof.

5. The apparatus of claim 4, wherein the apparatus comprises the cluster beam apparatus and wherein the aerodynamic lens reduces particle losses between a high-pressure cluster-producing surrounding and a low-pressure cluster-beam surrounding.

6. The apparatus of claim 1, wherein the aperture is circular or rectangular.

7. The apparatus of claim 1, wherein the apparatus comprises at least two aerodynamic lenses.

8. The apparatus of claim 1, wherein the aerodynamic lens aerodynamically focuses particles within a selected range of products of particle density and particle diameter below about 20 nm·g/cm$^3$.

9. The apparatus of claim 8, wherein the selected range includes products of particle density and particle diameter of about 15 nm·g/cm$^3$.

10. The apparatus of claim 8, wherein the selected range includes products of particle density and particle diameter of about 3 nm·g/cm$^3$.

11. The apparatus of claim 10, wherein the particles have a density higher than one gram per cm$^3$ and wherein the selected range includes products of particle density and particle diameter below about 3 nm·g/cm$^3$.

12. A method of designing an apparatus including an aerodynamic lens disposed in a tube for shaping an aerosol beam, the method comprising:
    obtaining a relationship between i) a product of particle density and particle diameter of particles suspended in the aerosol beam, ii) an operating pressure for the aerodynamic lens, and iii) a size of an aperture in the aerodynamic lens;
    selecting, using the relationship, the operating pressure to provide subsonic continuum flow of the aerosol beam through the aerodynamic lens at least for particles where a product of particle density and particle diameter is below about 20 nm·g/cm$^3$; and
    selecting the aperture size using the relationship.

13. The method of claim 12, wherein the aerodynamic lens is configured to operate at a suboptimal or optimal Stokes number.

14. The method of claim 12, wherein the operating pressure is selected such that it exists above a Mach limit pressure and above a Knudsen limit pressure.

15. The method of claim 12, further comprising selecting an inner diameter for spacers in the tube, the inner diameter being several times the aperture size.

16. The method of claim 12, further comprising reducing a spacer length to reduce particle residence time and particle diffusion.

17. The method of claim 12, wherein particle diffusion is taken into account in selecting the operating pressure.

18. The method of claim 12, wherein selecting the operating pressure comprises identifying a maximum operating pressure at which a rate of particle diffusion is minimized.

19. The method of claim 12, wherein selecting the operating pressure or aperture size comprises selecting 1) a carrier gas with minimum possible molecular weight or 2) a mixture of different carrier gases with minimum possible molecular weight.

20. A method of designing an apparatus including an aerodynamic lens disposed in a tube for shaping an aerosol beam having particles suspended in a gas, the method comprising:
    selecting a particle size range, a particle density for the particles, and an aerosol mass flow rate;
    calculating a maximum operating pressure for the apparatus that provides a laminar continuum flow of the gas for at least some particles where a product of particle density and particle diameter is below about 20 nm·g/cm$^3$;
    calculating a size for an aperture in the aerodynamic lens using the maximum operating pressure; and
    selecting an inner diameter and lengths of spacers for the apparatus.

21. The method of claim 20, wherein calculating the maximum operating pressure comprises a step selected from the group consisting of: solving equations for the laminar continuum flow and for particle focusing, identifying an intersection of graphs in a diagram, and combinations thereof.

22. The method of claim 21, wherein the step provides a calculated pressure and wherein calculating the maximum operating pressure comprises reducing the calculated pressure by a predefined amount.

23. The method of claim 20, further comprising selecting 1) a carrier gas with minimum possible molecular weight or 2) a mixture of different carrier gases with minimum possible molecular weight, and performing the steps of calculating the maximum operating pressure and the aperture size for the lighter carrier gas or the mixture of different carrier gases.

24. The method of claim 20, wherein calculating the maximum operating pressure comprises selecting a lower Stokes number for the particles upon determining that the maximum operating pressure does not provide continuum flow of the gas.

25. The method of claim 20, further comprising decreasing the mass flow rate, upon determining that flow through the aerodynamic lens is not laminar, and thereafter calculating a new maximum operating pressure and lens dimension using the decreased mass flow rate.

26. An apparatus for shaping an aerosol beam having particles suspended in a gas, the apparatus comprising:
    several aerodynamic lenses adapted to focus at least some particles where a product of particle density and particle diameter is below about 20 nm·g/cm$^3$, each of the aerodynamic lenses having an aperture therethrough, wherein sizes of the apertures and an operating pressure are selected so that each of the aerodynamic lenses aerodynamically focuses substantially all of the particles.

27. The apparatus of claim 26, wherein the sizes of the apertures and the operating pressure are selected using a predefined relationship that involves at least a mass flow rate of a carrier gas, particle properties, and a Stokes number.

28. The apparatus of claim 26, wherein the aerodynamic lenses are adapted so that they aerodynamically focus particles within a predefined particle density and particle diameter product range below about 20 nm·g/cm$^3$.

29. The apparatus of claim 28, wherein the predefined particle density and particle diameter product range is one selected from the group consisting of:

a) a small band below about 20 nm·g/cm$^3$; b) a large band below about 20 nm·g/cm$^3$; c) 9-11 nm·g/cm$^3$; and d) 3-20 nm·g/cm$^3$.

30. The apparatus of claim 26, wherein the aerodynamic lenses operate at a suboptimal Stokes number.

31. The apparatus of claim 26, wherein the aerodynamic lenses are identical.

32. An apparatus for shaping an aerosol beam having particles suspended in a gas, the apparatus comprising:

an aerodynamic lens having an aperture therethrough, wherein a size of the aperture and an operating pressure of the aerodynamic lens are selected so that aerodynamic lens aerodynamically focuses particles where a product of particle density and particle diameter is at most about 10 nm·g/cm$^3$.

33. The apparatus of claim 1, wherein the aperture, the operating pressure and the particle diameter and density satisfy a relationship providing that:

$$\rho_p d_p = \left(1 + \frac{\pi\alpha}{8}\right)\sqrt{2\pi\gamma^3}\, St_o \frac{p_1^2 d_f^3}{\dot{m}c^3}$$

wherein
$\alpha$=a momentum accommodation coefficient;
$\gamma$=a ratio of specific heats of the gas;
$\dot{m}$=a mass flowrate of the gas;
$\rho_p$=the particle density;
$d_p$=the particle diameter;
c=speed of sound in the gas at a temperature upstream of the aerodynamic lens;
$d_f$=the aperture size;
$St_o$=Stokes number for the particles; and
$p_1$ =operating pressure.

34. The method of claim 12, wherein the relationship is:

$$\rho_p d_p = \left(1 + \frac{\pi\alpha}{8}\right)\sqrt{2\pi\gamma^3}\, St_o \frac{p_1^2 d_f^3}{\dot{m}c^3}$$

wherein
$\alpha$=a momentum accommodation coefficient;
$\gamma$=a ratio of specific heats of the gas;
$\dot{m}$=a mass flowrate of the gas;
$\rho_p$=the particle density;
$d_p$=the particle diameter;
c=speed of sound in the gas at a temperature upstream of the aerodynamic lens;
$d_f$=the aperture size;
$St_o$=Stokes number for the particles; and
$p_1$ =operating pressure.

* * * * *

UNITED STATES PATENT AND TRADEMARK OFFICE
CERTIFICATE OF CORRECTION

PATENT NO. : 7,476,851 B2  Page 1 of 1
APPLICATION NO. : 11/269932
DATED : January 13, 2009
INVENTOR(S) : Xiaoliang Wang et al.

It is certified that error appears in the above-identified patent and that said Letters Patent is hereby corrected as shown below:

Title Page, item (75), Inventors, please delete "Einar Kruis" and insert --Frank Einar Kruis-- therefor;

Column 33, line 15 (Claim 1), after "that" please insert --the--;

Column 35, line 29 (Claim 32), after "that" please insert --the--.

Signed and Sealed this

Twenty-eighth Day of April, 2009

JOHN DOLL
*Acting Director of the United States Patent and Trademark Office*